United States Patent
Degen et al.

(10) Patent No.: US 11,072,643 B2
(45) Date of Patent: Jul. 27, 2021

(54) FUSION PROTEIN

(71) Applicant: ADVANCECOR GMBH, Martinsried (DE)

(72) Inventors: Heidrun Degen, Martinsried (DE); Silvia Goebel, Martinsried (DE); Kristin Adler, Martinsried (DE); Martin Ungerer, Martinsried (DE)

(73) Assignee: ADVANCECOR GMBH, Martinsried (DE)

( * ) Notice: Subject to any disclaimer, the term of this patent is extended or adjusted under 35 U.S.C. 154(b) by 0 days.

(21) Appl. No.: 16/628,250

(22) PCT Filed: Jul. 3, 2018

(86) PCT No.: PCT/EP2018/067952
§ 371 (c)(1),
(2) Date: Jan. 2, 2020

(87) PCT Pub. No.: WO2019/007959
PCT Pub. Date: Jan. 10, 2019

(65) Prior Publication Data
US 2020/0216513 A1   Jul. 9, 2020

(30) Foreign Application Priority Data
Jul. 3, 2017 (EP) .................................. 17179344

(51) Int. Cl.
*C07K 14/705* (2006.01)
*C07K 14/78* (2006.01)
*A61K 39/395* (2006.01)
*C12N 9/64* (2006.01)
*C12R 1/01* (2006.01)

(52) U.S. Cl.
CPC ...... *C07K 14/705* (2013.01); *C07K 14/70596* (2013.01); *C12R 1/01* (2013.01); *C07K 2319/30* (2013.01)

(58) Field of Classification Search
CPC .... C12N 9/6432; C12N 9/6437; C12N 9/644; C12N 9/647
See application file for complete search history.

(56) References Cited

PUBLICATIONS

Ungereretal., European Heart Journal, 35, SUPPL. 1, pp. 1170-1171, abstract No. P6507, Sep. 2014.*

* cited by examiner

*Primary Examiner* — Maryam Monshipouri
(74) *Attorney, Agent, or Firm* — Adriano & Associates

(57) ABSTRACT

The present invention relates to a fusion protein selectively binding collagen and having ectonucleotidase activity. The fusion protein comprises an amino acid sequence of the extracellular domain of glycoprotein VI fused via a first linker sequence to the N-terminus of an amino acid sequence of an Fc region, whereby the C-terminus of the Fc region is linked via a second linker sequence to an amino acid sequence of the extracellular domain of a CD39 protein.
The fusion protein is useful in the treatment or prevention of cardiovascular disease or diabetes, such as in the treatment of acute atherothrombotic events with a favorable risk-benefit ratio.

12 Claims, 6 Drawing Sheets
Specification includes a Sequence Listing.

ized by local release of adenosine diphosphate (ADP), several cytokines and other biologically active substances
FUSION PROTEIN This application is a 371 application of PCT application No. PCT/EP2018/067952, filed Jul. 3, 2018, which claims the priority of EP Serial No. 17179344.1, filed Jul. 3, 2017, the contents of all of which are hereby incorporated by reference in their entireties into the present application.

FIELD OF THE INVENTION

The present invention relates to a fusion protein. Specifically, the present invention relates to a fusion protein selectively binding collagen and having ectonucleotidase activity. Moreover, the present invention relates to a polynucleotide comprising a nucleotide sequence that encodes a fusion protein according to the present invention. Furthermore, the present invention relates to an expression vector comprising a promoter operably associated with the polynucleotide of the present invention, and a host cell line transformed or transfected with the polynucleotide of the present invention. The present invention also relates to a pharmaceutical composition comprising the fusion protein of the present invention. Finally, the present invention relates to a process for the preparation of the fusion protein of the present invention.

The fusion protein of the present invention provides local antithrombotic activity at sites of atherosclerotic plaque rupture or injury. Therefore, the fusion protein of the present invention is useful in a method for the treatment of the human or animal body by therapy or a diagnostic method practiced on the human or animal body, in particular in the treatment or prevention of cardiovascular disease or diabetes, such as the treatment of acute atherothrombotic events with a favorable risk-benefit ratio.

BACKGROUND OF THE INVENTION

Stroke and myocardial infarction are leading causes of death (1). Ischemic stroke is the most frequent disabling disease. Frequently, the underlying alteration is the rupture or erosion of atherosclerotic plaques which leads to platelet adhesion and thrombus formation, and to embolization, as observed in cerebral arteries (2).

Glycoprotein VI (GPVI)-mediated and collagen-bound von Willebrand Factor (vWF)-dependent platelet adhesion and activation play important roles in human plaque-triggered thrombus formation and subsequent development of cardiovascular syndromes such as stroke (3-6). GPVI expression is specifically observed in platelets and megakaryocytes (7, 8).

The interaction of GPVI with collagen can be inhibited competitively by a dimeric GPVI-Fc fusion protein (Revacept®)(9, 10) or by antibodies which have been developed to block GPVI (11-13).

Dimeric soluble glycoprotein VI (GPVI-Fc) inhibits platelet-induced thrombus formation at sites of vascular injury (9). Administration of GPVI-Fc improves myocardial ischemia (33) and cerebral infarction (34) without affecting bleeding time (35), and inhibits progression of atherosclerosis (36). GPVI-Fc also inhibits collagen-induced aggregation in humans in a phase I study (10). GPVI-Fc acts locally at the site of plaque rupture, and is most effective under high shear flow (12). Dimeric GPVI-Fc (Revacept®) binds to GPVI binding sites on plaque collagen without increasing bleeding in clinical studies. GPVI-Fc is a potent inhibitor of atherosclerotic plaque-induced platelet aggregation at high shear flow, but its inhibition at low shear flow is limited.

Anti-GPVI antibodies are systemic and potent inhibitors of plaque- and collagen-induced platelet aggregation in static and dynamic models. Anti-GPVI antibodies increase bleeding propensity as observed in some patients with anti-GPVI auto-antibodies (13), whereas GPVI-Fc does not interact directly with platelets, does not increase bleeding times in clinical studies and may therefore be safer (10). Therefore, GPVI-Fc circumvents important shortcomings of existing platelet inhibitors and antithrombotics, which all incur a moderate to strongly increased bleeding risk (14, 15).

Sites of platelet adhesion and aggregation are characterized by local release of adenosine diphosphate (ADP), several cytokines and other biologically active substances from these platelets (16). Released ADP activates additional platelets and leads to further platelet aggregation and secretion, and thrombus propagation (16).

Ecto-nucleotidase CD39 inhibits local adenosine diphosphate (ADP) accumulation at vascular plaques. Specifically, the endothelial ecto-ADPase CD39/ENTPDase1 degrades ADP to AMP and Pi and thus locally inactivates an important platelet stimulus which may cause occlusive thrombi (17-19).

Gayle et. al. developed a soluble form of CD39 which can inhibit platelet function in vitro (20) and in vivo (17, 21). Hence, the potential of each, soluble CD39 and soluble GPVI (GPVI-Fc) alone to inhibit platelet function has been characterized. A general, non-specific CD39 activation, however, results in a bleeding propensity both in CD39-transgenic mice (22) and after systemic application of soluble CD39 in vivo (23).

So far, dual antiplatelet therapy which typically combines acetylsalicylic acid (ASA) with an ADP receptor antagonist such as clopidogrel is the standard therapy for patients with acute vascular lesions treated by coronary stenting, and its major limitation is increased bleeding risk.

SUMMARY OF THE INVENTION

It is a problem of the present invention to provide a fusion protein having local antithrombotic activity at sites of atherosclerotic plaque rupture or injury for inhibiting plaque-induced platelet aggregation at high and low shear flow, while lacking any systemic bleeding risk, which fusion protein is useful in the treatment or prevention of cardiovascular disease or diabetes, such as the treatment of acute atherothrombotic events with a favorable risk-benefit ratio.

Moreover, it is a problem of the present invention to provide a polynucleotide comprising a nucleotide sequence that encodes the fusion protein according to the present invention, in particular an expression vector for preparing the fusion protein of the present invention.

It is a further problem of the present invention to provide a host cell for efficiently producing the fusion protein according to the present invention.

It is a further problem of the present invention to provide a pharmaceutical composition for treating or preventing cardiovascular disease or diabetes, such as the treating of acute atherothrombotic events with a favorable risk-benefit ratio.

Finally, it is the problem of the present invention to provide a process for the preparation of the fusion protein of the present invention.

The fusion protein of the present invention is useful in a method for the treatment of the human or animal body by therapy or a diagnostic method practiced on the human or animal body, in particular in the treatment or prevention of cardiovascular disease or diabetes, such as the treatment of acute atherothrombotic events with a favorable risk-benefit ratio.

Accordingly, the present invention provides a lesion-directed dual antiplatelet therapy. Specifically, the present invention provides a fusion protein selectively binding collagen and having ectonucleotidase activity, which comprises an amino acid sequence of the extracellular domain of glycoprotein VI fused via a first linker sequence to the N-terminus of an amino acid sequence of an Fc region, whereby the C-terminus of the Fc region is linked via a second linker sequence to an amino acid sequence of the extracellular domain of a CD39 protein.

Moreover, the present invention provides a polynucleotide comprising a nucleotide sequence that encodes a fusion protein of the present invention.

Moreover, the present invention provides an expression vector comprising a promoter operably associated with the polynucleotide of the present invention.

The present invention also provides a host cell line transformed or transfected with a polynucleotide of the present invention.

The present invention also provides a pharmaceutical composition comprising the fusion protein of the present invention, and a pharmaceutically acceptable carrier.

Furthermore, the present invention provides a fusion protein of the present invention for use in a method for the treatment of the human or animal body by therapy or a diagnostic method practiced on the human or animal body.

Furthermore, the present invention provides a fusion protein of the present invention for use in the treatment or prevention of cardiovascular disease or diabetes.

Finally, the present invention provides a process for the preparation of a fusion protein, which comprises:

(a) transforming a host cell comprising at least one vector of claim 9;

(b) culturing the transformed host cell in suitable conditions for expression of the fusion protein; and (c) isolating the fusion protein.

The present invention is based on the recognition that the local antithrombotic activity at sites of atherosclerotic plaque rupture or injury of Revacept® may be extended so that plaque-induced platelet aggregation may be efficiently and effectively inhibited also at low shear flow, while systemic bleeding risks may be avoided by combining soluble CD39 and GPVI-Fc to form a recombinant, bifunctional GPVI-CD39 fusion protein. The fusion protein of the present invention potently inhibits collagen- and plaque-induced platelet thrombus formation in vitro and arterial thrombus formation after vascular injury in vivo. The fusion protein according to the present invention can bind to vascular lesions locally and concentrate in plaques, which allows for markedly lower effective doses than soluble CD39, thus minimizing its bleeding propensity.

The recombinant fusion protein of the present invention includes a GPVI domain coupled to an ecto-ADPase CD39 that degrades prothrombotic extracellular ADP (17, 18). The fusion protein of the present invention efficiently inhibits ADP-, collagen- and human plaque-induced platelet aggregation under static conditions, and plaque-triggered platelet adhesion and thrombus formation under arterial flow at clinically relevant concentrations. In contrast, collagen/epinephrine-triggered closure times as measured in a PFA-200 device were unchanged, because epinephrine is a sufficiently strong agonist. Moreover, GPVI-CD39 markedly delayed ferric chloride-induced thrombus formation in mice in vivo, but did not prolong tail bleeding times in vivo at any doses.

The fusion protein of the present invention provides a novel lesion-directed dual antiplatelet therapy (inhibition of collagen- and ADP-induced platelet adhesion/aggregation) at sites of arterial vulnerability (e.g. plaque ruptures and erosions, stented lesions), without incurring a relevant systemic bleeding risk.

Endothelial ecto-ADPase CD39/ENTPDase1 degrades ADP to AMP and Pi and thus inactivates an important agent which may cause occlusive thrombi (17-19). Transgenic mice which overexpressed CD39 showed impaired platelet aggregation, resistance to thrombogenic stimuli, but also markedly prolonged tail bleeding time which led to death when unchecked (22). Similarly, these CD39-transgenic mice were also resistant to ferric chloride-induced thrombus formation (28), and to myocardial injury (29). Also CD39-transgenic pigs were generated and subjected to a model of myocardial ischemia-reperfusion injury by LAD balloon inflation (30). These pigs showed markedly reduced infarct sizes compared to wild-type controls. In contrast, CD39−/− knockout mice were characterized by increased cerebral infarct volumes and reduced postischemic cerebral perfusion (31). These knockout mice also developed increased atherosclerotic plaque burden when cross-bred with ApoE−/− knockouts, with especially low CD39 expression in atheroprone regions (32).

Gayle et. al. developed a soluble form of CD39 which can inhibit platelet function in vitro (20) and in vivo (18, 21, 31): administration of 4 mg/kg soluble CD39 led to clearly reduced infarct sizes and improved neurological function in experimental mouse stroke (whereas 1 mg/kg had no effects). In this study, bleeding time was only prolonged after administration of 8 mg/kg or higher doses of soluble CD39 in mice. Also Hohmann et al. reported markedly increased bleeding time after 8 mg/kg, but not after 0.8 mg/kg (23). However, this lower dose did not have a beneficial effect on occlusion time in a ferric chloride-induced carotid thrombosis model (23). In pigs, 700 µg/kg soluble CD39 increased bleeding times, but only achieved a non-significant trend to attenuate platelet and fibrin deposition after coronary balloon injury (21).

The combination of GPVI-Fc with CD39 potentiates the antithrombotic effect of GPVI-Fc by blocking not only the primary platelet agonist collagen, but also the secondary agonist ADP. Local platelet release of ADP is an important mediator of atherosclerotic plaque-stimulated platelet aggregation at static and flow conditions (19). GPVI-coupled CD39 should concentrate specifically at collagen fibers within vascular lesions and atherosclerotic plaques, and hence act at lower local concentrations in response to lower systemic concentrations than soluble recombinant CD39. Thus, bleeding risk which results from recombinant CD39 will be minimized (23, 20).

Under flow, platelet inhibition by GPVI-CD39 is surprisingly more pronounced than adding a full ex vivo dose of the ADP receptor inhibitor ticagrelor to GPVI-Fc: Comparing the results of the current study with those of our previous results (37,38), it occurred that 150 nM GPVI-CD39 were equally effective in inhibiting plaque-induced platelet aggregation (81% inhibition) as the combination of 150 nM GPVI-Fc with 3.82 µM of the ADP receptor antagonist ticagrelor (79% inhibition). This comparison underlines the relative potency of the GPVI-CD39 fusion protein of the present invention compared to existing antiplatelet drugs. Similar to previous reports on solCD39(21, 23), the fairly low dose of GPVI-CD39 used in this study had no effect on systemic bleeding times. However, GPVI-CD39 was fully effective in inhibiting arterial thrombosis in response to a ferric chloride challenge. This finding implies that the combination of CD39 with GPVI in a single molecule offers a favourable risk-benefit ratio.

The present invention focuses on local enrichment of CD39 functionality at high-risk arterial lesion before a full thrombus has evolved. Such local enrichment of CD39 provides an attractive alternative therapeutic option in arterial diseases, since it was recently shown that reduced CD39 activity was associated with disease progression in patients with peripheral arterial disease (40). However, the frequently used ADP receptor antagonist drug clopidogrel, and ticlopidin further inhibit CD39 activity especially at the beginning (the first days) of the respective therapies (41), so that in comparison, short-term rapid intravenous administration of GPVI-CD39 might be especially beneficial in acute vascular syndromes and emergency conditions.

Generally, CD39 fusion proteins offer perspectives in several regards and indications (42). CD39 has been proposed as an approach to widen the cardiovascular therapeutic window (43). The present invention demonstrates that the anti-atherosclerotic properties of blocking GPVI binding sites and promoting CD39 activity add up at the site of atherothrombosis when combined in a bifunctional molecule, but that this fusion protein does not compromise systemic hemostasis.

A: Structure (left panel) and putative 3D-modelling (right panel) of bifunctional, recombinant GPVI-CD39 compared to GPVI-Fc. The 3D model shows the extracellular GPVI domains in blue, the Fc part in green, and the CD39 domain in light red. The N-terminal leader peptides of each protein are cleaved before secretion of each protein.

B: Coomassie staining of GPVI-CD39 as purified from supernatants of GPVI-CD39-expressing cells (left column, nr: non-reducing conditions; right column, r: reducing conditions).

C: Specific ADPase activity of recombinant GPVI-CD39 (333 nmol/L) in comparison to that of commercially available soluble CD39 (666 nmol/L) (n=3, mean±SEM). Both specific activities were determined at other enzyme molarities and did not differ, as expected, because substrate concentrations were not limiting.

Figure 2:
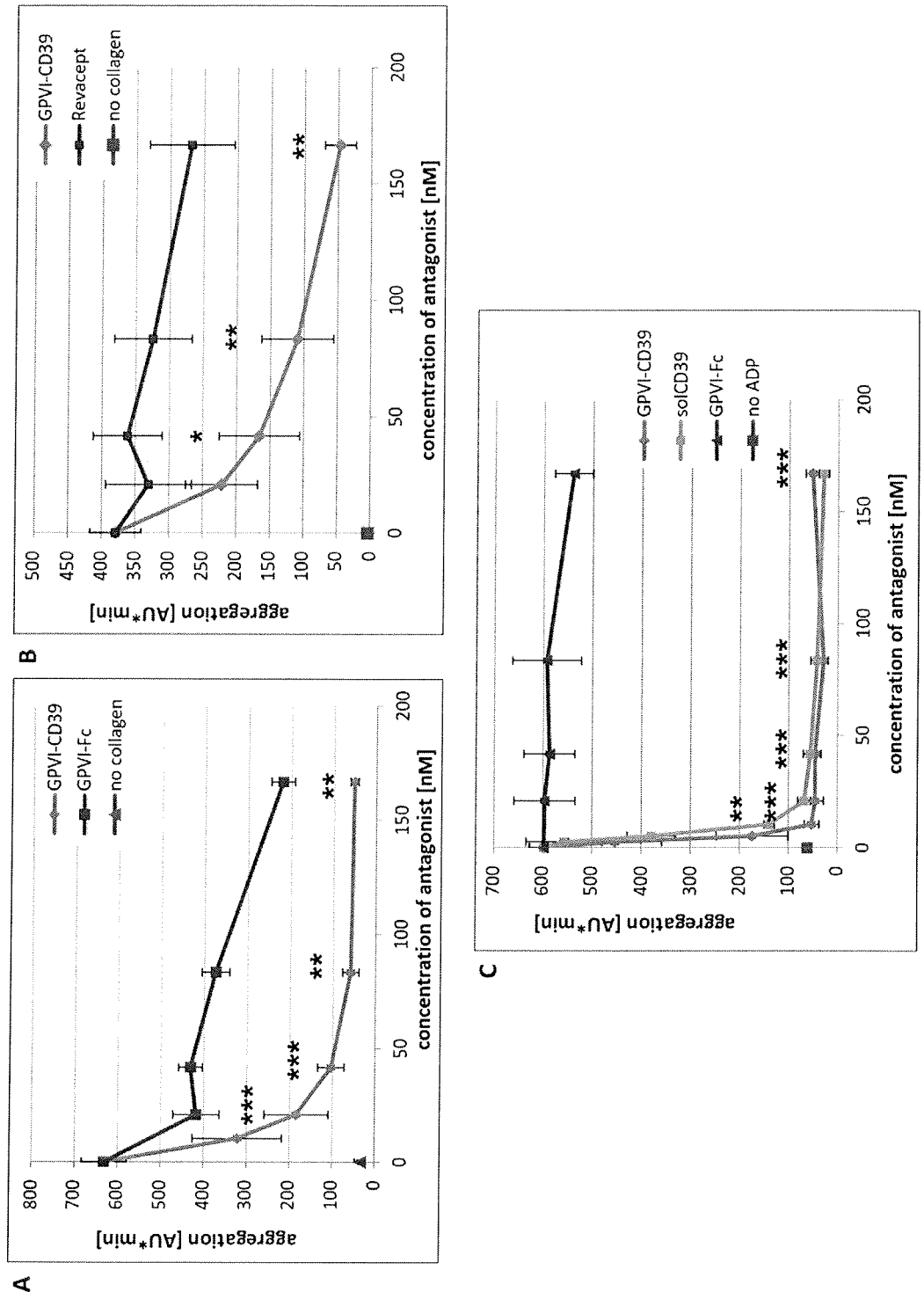

FIG. 2 shows the effects of GPVI-CD39 and GPVI-Fc fusion proteins, and of control proteins on static platelet aggregation in blood after stimulation with collagen or ADP. Platelet aggregation was determined by impedance aggregometry. Values are means+/−SEM.

A: Platelet aggregation after stimulation with 12 µg/mL collagen extracted from rabbit aorta. Pre-incubation with increasing concentrations of GPVI-CD39 reduces platelet aggregation more strongly than GPVI-Fc alone (n=5; p<0.01 and *p<0.001 as compared to GPVI-Fc).

B: Platelet aggregation after stimulation with 103 µg/ml collagen from cultured human fibroblasts (VitroCol), as determined by impedance aggregometry. Pre-incubation with increasing concentrations of GPVI-CD39 reduces platelet aggregation more strongly than GPVI-Fc alone (n=5; *p<0.05 and **p<0.01 as compared to GPVI-Fc).

C: Platelet aggregation after stimulation with 6.5 µmol/L ADP. Pre-incubation with increasing concentrations of either GPVI-CD39 (n=8) or of soluble CD39 markedly reduces ADP-induced platelet aggregation, whereas GPVI-Fc alone has no effect (p<0.01 and *p<0.001).

Figure 3:
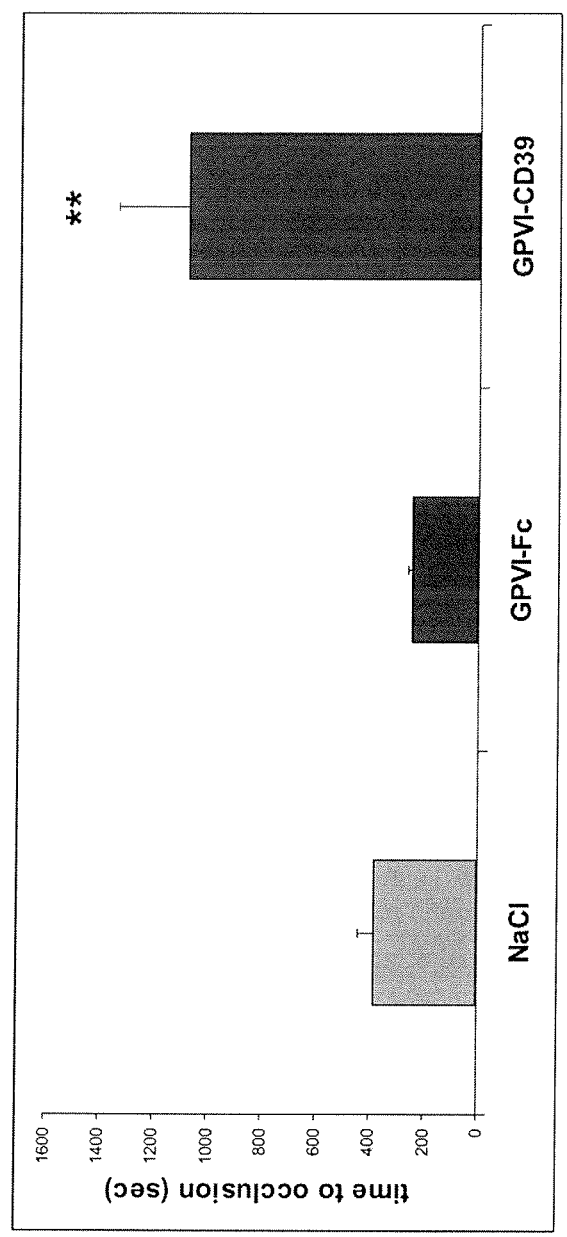

FIG. 3 shows the effect on thrombus formation after ferric chloride injury: mean times to occlusion after administration of vehicle (NaCl), GPVI-Fc or GPVI-CD39

Administration of 3 mg/kg (10 nmol/kg) GPVI-CD39 strongly delayed ferric chloride-induced thrombus formation in vivo, as compared to administration of 1.5 mg/kg (10 nmol/kg) GPVI-Fc or vehicle only. Mean values of 7 independent experiments are shown with SEM. **p<0.01 by ANOVA.

Figure 4:
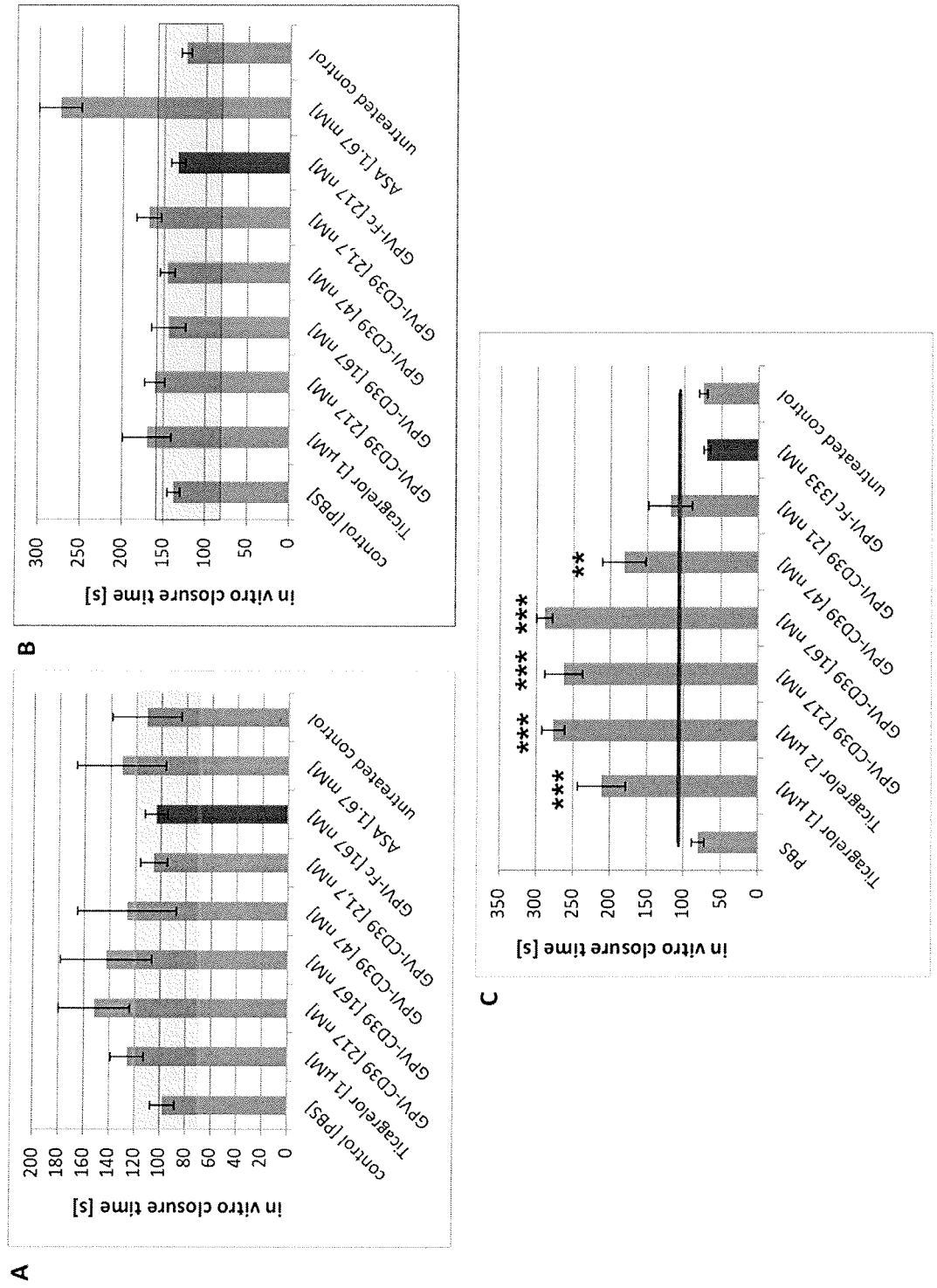

FIG. 4 shows the effects on PFA 200 closure times of human blood ex vivo

A: Effects of ticagrelor, GPVI-CD39, GPVI-Fc or ASA at the indicated concentrations on closure times in collagen/ADP cartridges (n=8 samples from independent donors). No significant differences between groups occurred.

B: Effects of ticagrelor, GPVI-CD39, GPVI-Fc or ASA at the indicated concentrations on closure times in collagen/epinephrine cartridges (n=8 samples from independent donors). No significant differences between results for GPVI-CD39 and GPVI-Fc occurred. Closure time was significantly (p=0.04) prolonged after addition of ASA compared to buffer PBS only.

C: Effects of ticagrelor, GPVI-CD39, GPVI-Fc or ASA at the indicated concentrations on closure times in specific P2Y cartridges (n=8 samples from independent donors; p<0.01 and *p<0.001 versus PBS only).

Figure 5:
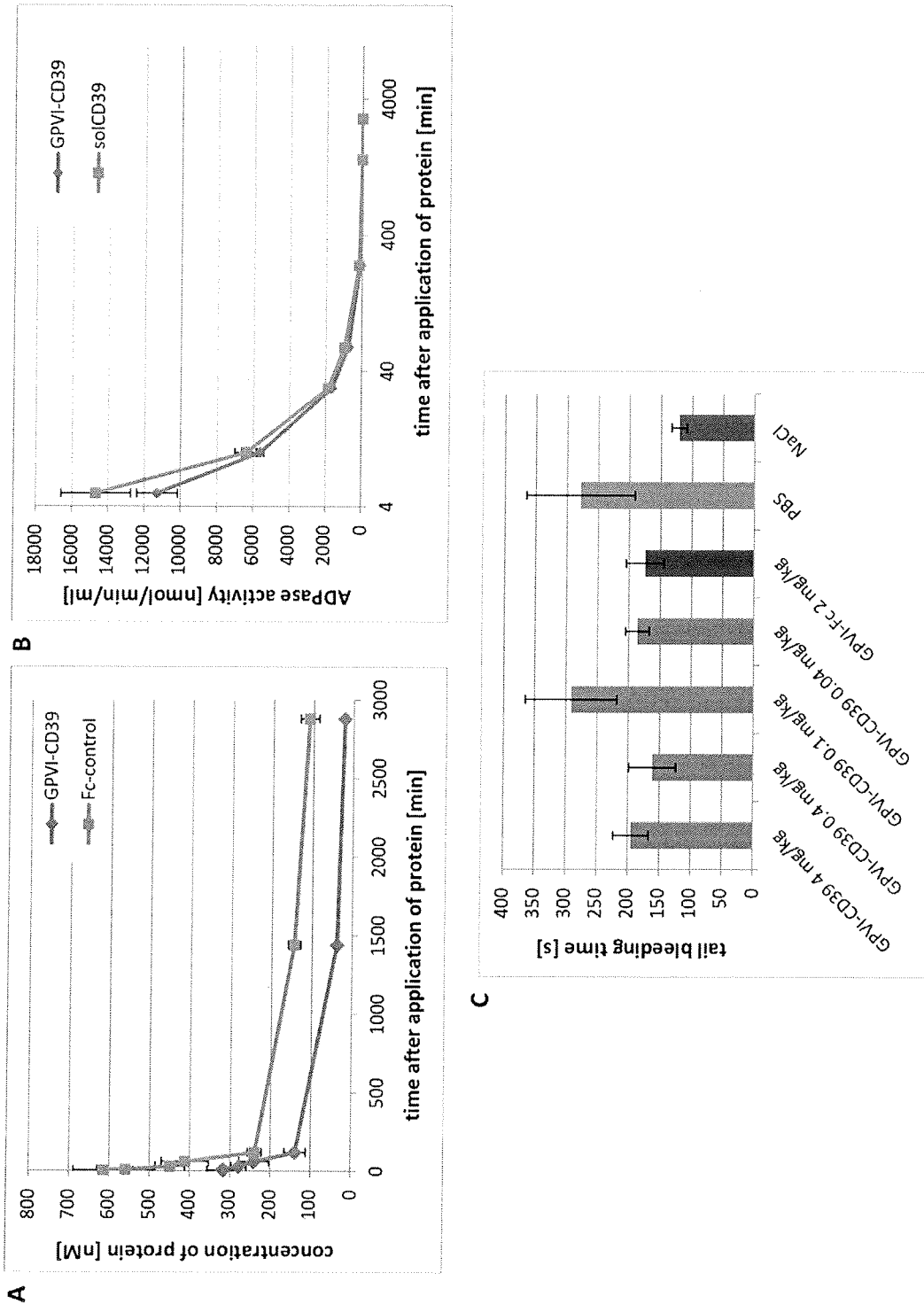

FIG. 5 shows the results of a pharmacokinetic and pharmacodynamic evaluation in mice in vivo; bleeding times in vivo.

A: plasma concentrations in mice up to 48 hours after administration of GPVI-CD39 or Fc control protein.

Blood samples were taken at the indicated times after IV administration of 4 mg/kg (13 nmol/kg) GPVI-CD39, and plasma levels were detected by ELISA. Means+/−SEM are shown. (n=3 animals).

B: ADPase activities in mice up to 48 hours after administration of GPVI-CD39 or Fc controls.

Blood samples were taken at the indicated times after IV administration of either 4 mg/kg GPVI-CD39 (13 nmol/kg, corresponding to 26 nmol/kg ADPase moieties) or 26 nmol/kg solCD39, and ADP turnover (means+/−SEM) was measured by using a malachite green phosphate detection kit. Time is shown at a logarithmic scale to visualise decrease in activity during early time points (n=3 animals).

C: tail bleedings times

Tails were incised 15 minutes after IV administration of the indicated doses of GPVI-CD39, GPVI-Fc or buffer, and tail bleeding times were determined.

Mean values of 8 independent experiments are shown with SEM. No significant differences between groups occurred.

Figure 6:
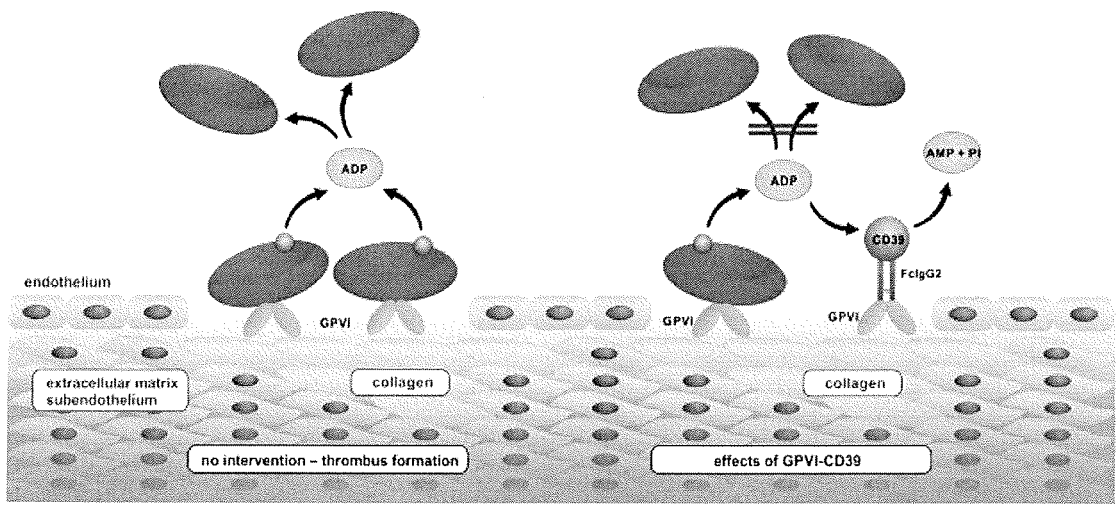
Figure 6:
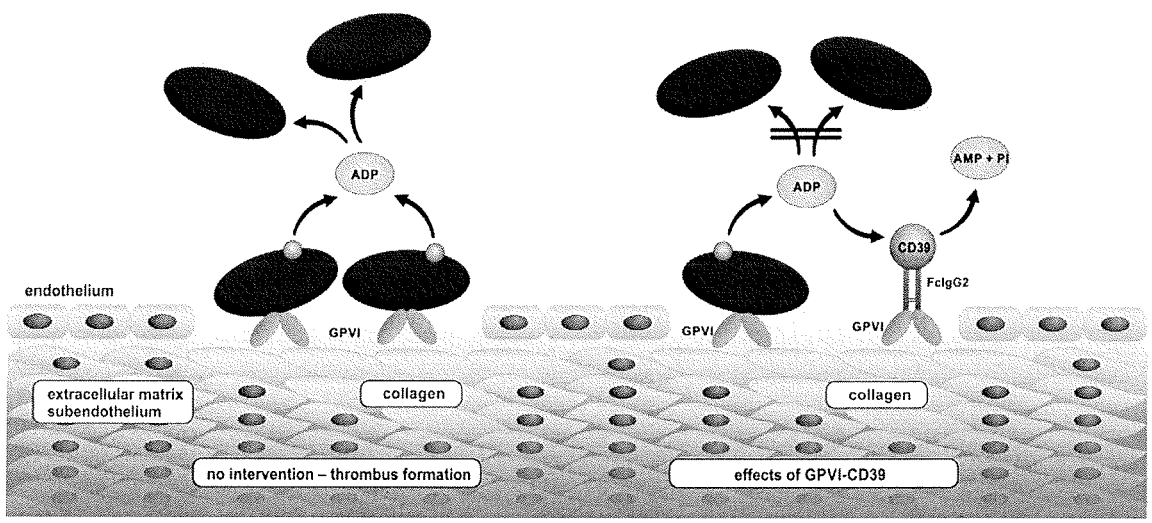

FIG. 6 shows a schematic representation of the mode of action of GPVI-CD39 at arterial plaques.

DETAILED DESCRIPTION OF THE INVENTION

The present invention relates generally to fusion proteins, polynucleotides encoding fusion proteins, and describes methods of treating, preventing, or ameliorating diseases or disorders using fusion proteins.

Definitions

The following definitions are provided to facilitate understanding of certain terms used throughout this specification.

As used herein, "fusion protein" refers to a protein formed by fusing the N-terminus of at least one molecule of an Fc portion (or fragment or variant thereof) via a first linker head-to-tail to at least one molecule of the extracellular domain of glycoprotein VI (or a fragment or variant thereof) and the C-terminus of at least one molecule of an Fc portion (or fragment or variant thereof) head-to-tail via a second linker to an extracellular domain of a CD39 protein (or fragment or variant thereof). A fusion protein of the invention comprises an amino acid sequence selected from (a) the amino acid sequence of SEQ ID NO: 1; (b) a variant of (a) which is at least 90% identical to the amino acid sequence of SEQ ID NO: 1, wherein said variant selectively binding collagen and having ectonucleotidase activity; (c) a fragment wherein said fragment selectively binding collagen and having ectonucleotidase activity and comprising the amino acid sequence of SEQ ID NO: 2, 3, or 4, or a variant the amino acid sequence of which is at least 90% identical to the amino acid sequence of SEQ ID NO: 2, 3, or 4, or (d) a fusion protein expressed by the cell line GPVI-Fc-linker-CD39 as deposited with Leibniz-Institut DSMZ. The GPVI, Fc and CD39 portions and the first and second linker of the fusion protein of the present invention are associated with one another by genetic fusion, whereby the fusion protein is generated by translation of a nucleic acid in which a polynucleotide encoding all or a portion of an extracellular domain of GPVI, is joined in-frame with a polynucleotide encoding a first linker, an Fc portion, a second linker, and CD39 portions.

A fusion protein of the invention may be processed by a host cell and secreted into the culture medium. Processing of the nascent fusion protein that occurs in the secretory pathways of the host cell may include signal peptide cleavage, assembly into dimeric proteins, formation of disulfide bonds, proper folding, and addition and processing of carbohydrates by N- and O-linked glycosylation. A fusion protein of the invention is preferably in the processed form. The "processed form of a fusion protein" refers to a fusion protein product which has undergone N-terminal signal peptide cleavage ("mature fusion protein").

As used herein, "polynucleotide" refers to a nucleic acid molecule having a nucleotide sequence encoding a fusion protein comprising at least one molecule of the extracellular domain of glycoprotein VI (or a fragment or variant thereof) joined in frame via a first linker sequence to an Fc portion (or fragment or variant thereof), joined in frame via a second linker sequence to an extracellular domain of a CD39 protein (or fragment or variant thereof); a nucleic acid molecule having a nucleotide sequence encoding a fusion protein comprising the amino acid sequence of SEQ ID NO: 1 or a fragment or variant thereof; a nucleic acid molecule having a nucleotide sequence comprising the sequence shown in SEQ ID NO:6; a nucleic acid molecule having a nucleotide sequence encoding a fusion protein comprising the amino acid sequence of SEQ ID NO: 2, 3, 4, or 5; a nucleic acid molecule having a nucleotide sequence encoding a fusion protein of the invention generated as described in the Examples; a nucleic acid molecule having a nucleotide sequence encoding a fusion protein of the invention; or a polynucleotide having a nucleotide sequence contained in a fusion construct in the cell line CHO GPVI-Fc-linker-CD39 as deposited with Leibniz-lnstitut DSMZ.

As used herein, "fusion construct" refers to a nucleic acid molecule comprising, a polynucleotide according to the present invention and further comprising one or more of the following elements: (1) a region for initiation of transcription (e.g., a promoter region, such as for example, an inducible or regulable promoter, a constitutive promoter), (2) a functional self-replicating vector (including, for example, a shuttle vector, an expression vector, an integration vector, and/or a replication system), (3) a region for termination of transcription, (4) a leader sequence, and (5) a selectable marker.

By a fusion protein displaying a "therapeutic activity" or a fusion protein that is "therapeutically active" is meant a polypeptide fusion protein selectively binding collagen and having ectonucleotidase activity. As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture. Such in vitro or cell culture assays are commonly available as described in the art. Examples of assays include, but are not limited to those described herein in the Examples.

"A polypeptide having functional activity" refers to a polypeptide capable of displaying one or more known functional activities associated with the full-length, protein, and/or mature form of the fusion protein of the present invention. Such functional activities include, but are not limited to, biological activity, antigenicity, immunogenicity, ability to form multimers, and ability to bind to a receptor or ligand for a polypeptide.

"A polypeptide having biological activity" refers to a polypeptide exhibiting activity similar to, but not necessarily identical to, an activity of the fusion protein of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention.

A fusion protein of the present invention has at least one biological and/or therapeutic activity associated with the GPVI or CD39 protein portion (or fragment or variant thereof). The fusion proteins of the present invention can be assayed for therapeutic activity using or routinely modifying assays known in the art, as well as assays described in the Examples.

The term "variant" refers to a polynucleotide or polypeptide differing from a reference nucleic acid or polypeptide, but retaining essential properties thereof. Generally, variants are overall closely similar, and, in many regions, identical to a reference nucleic acid or polypeptide.

In a preferred embodiment, a fusion protein of the invention comprises (a) an amino acid sequence of the extracellular domain of human glycoprotein VI at least 75% identical to SEQ ID NO: 2;

(b) an amino acid sequence of an Fc region at least 75% identical to SEQ ID NO: 3;

(c) an amino acid sequence of a CD39 protein at least 75% identical to SEQ ID NO: 4; and/or (d) an amino acid sequence of the second linker at least 75% identical to SEQ ID NO: 5.

According to a further preferred embodiment, the second linker sequence of the fusion protein according to the present invention consists of at least five amino acid residues.

According to a further preferred embodiment the fusion protein of the present invention is a dimer.

According to a further preferred embodiment, the fusion protein according to the present invention has at least 90 percent identity with amino acid sequence of SEQ ID No.: 1.

Fusion proteins of the invention may be modified by glycosylation, i.e. the attachment of one or more oligosaccharide groups. Glycosylation can affect the physical properties of proteins and may have an effect on protein secretion, stability, and localization. Glycosylation occurs at specific locations along the polypeptide chain. Two major types of glycosylation may be distinguished: glycosylation forming O-linked oligosaccharides attached to serine or threonine residues, and glycosylation forming N-linked oligosaccharides attached to asparagine residues in an Asn-X-Ser or Asn-X-Thr sequence, where X can be any amino acid except proline. Protein structure and cell type may influence the number and nature of the carbohydrate units within the chains at different glycosylation sites. Glycosylation isomers are also common at the same site within a given cell type.

A fusion protein of the invention, as well as analogs and variants thereof, may be modified so that glycosylation at one or more sites is altered as a result of manipulation of their nucleic acid sequence, by the host cell in which they are expressed, or due to other conditions of their expression. For example, glycosylation isomers may be produced by abolishing or introducing glycosylation sites, e.g., by substitution or deletion of amino acid residues, such as substitution of glutamine for asparagine, or unglycosylated recombinant proteins may be produced by expressing the proteins in host cells that will not glycosylate them.

The GPVI proteins, CD39 proteins, Fc portion proteins, Revacept (GPVIFc), and nucleic acid and amino acid sequences are well known in the art and available in public databases such as GenBank, Chemical Abstracts Services Databases including the CAS Registry, and GenSeq published by Derwent). Exemplary nucleotide sequences of the GPVI proteins, CD39 proteins, Fc portion proteins, Revacept (GPVIFc), may be used to derive a polynucleotide of the invention. Sequences may be a wild type polynucleotide sequence encoding a given protein. Sequence may be a variant of said wild type polynucleotide sequence. Examples are polynucleotides encoding the wild type protein, wherein the DNA sequence has been optimized for expression in a particular species. Alternatively, variants may be polynucleotides encoding a variant of the wild type protein such as a site directed mutant or an allelic variant.

A preferred mature fusion protein according to the present invention is a fusion protein having an amino acid sequence of the following SEQ ID NO: 1.

QSGPLPKPSLQALPSSLVPLEKPVTLRCQGPPGVDLYRLEKLSSSRYQDQ

AVLFIPAMKRSLAGRYRCSYQNGSLWSLPSDQLELVATGVFAKPSLSAQP

GPAVSSGGDVTLQCQTRYGFDQFALYKEGDPAPYKNPERWYRASFPIITV

TAAHSGTYRCYSFSSRDPYLWSAPSDPLELVVTGTSVTPSRLPTEPPSSV

AEFSEATAELTVSFTNKVFTTETSRSITTSPKESDSPAGPARQYYTKGNG

GRVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNV

FSCSVMHEALHNHYTQKSLSLSPGKGGGGSGGGGSGGGGSTQNKALPENV

KYGIVLDAGSSHTSLYIYKWPAEKENDTGVVHQVEECRVKGPGISKFVQK

VNEIGIYLTDCMERAREVIPRSQHQETPVYLGATAGMRLLRMESEELADR

VLDVVERSLSNYPFDFQGARIITGQEEGAYGWITINYLLGKFSQKTRWFS

IVPYETNNQETFGALDLGGASTQVTFVPQNQTIESPDNALQFRLYGKDYN

VYTHSFLCYGKDQALWQKLAKDIQVASNEILRDPCFHPGYKKVVNVSDLY

KTPCTKRFEMTLPFQQFEIQGIGNYQQCHQSILELFNTSYCPYSQCAFNG

IFLPPLQGDFGAFSAFYFVMKFLNLTSEKVSQEKVTEMMKKFCAQPWEEI

KTSYAGVKEKYLSEYCFSGTYILSLLLQGYHFTADSWEHIHFIGKIQGSD

AGWTLGYMLNLTNMIPAEQPLSTPLSHST

The fusion protein of the present invention preferably contains an amino acid sequence of an extracellular portion of GPVI according to the following SEQ ID NO. 2.

SEQ ID NO.: 2
QSGPLPKPSLQALPSSLVPLEKPVTLRCQGPPGVDLYRLEKLSSSRYQDQ

AVLFIPAMKRSLAGRYRCSYQNGSLWSLPSDQLELVATGVFAKPSLSAQP

GRAVSSGGDVTLQCQTRYGFDQFALYKEGDPAPYKNPERWYRASFPIITV

TAAHSGTYRCYSFSSRDPYLWSAPSDPLELVVTGTSVTPSRLPTEPPSSV

AEFSEATAELTVSFTNKVFTTETSRSITTSPKESDSPAGPARQYYTKGN

The fusion protein of the present invention preferably contains an amino acid sequence of an Fc portion according to the following SEQ ID NO. 3.

SEQ ID NO.: 3
VECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVFS

CSVMHEALHNHYTQKSLSLSPGK

The fusion protein of the present invention preferably contains an amino acid sequence of an extracellular portion of a CD 39 protein according to the following SEQ ID NO. 4.

SEQ ID NO: 4
TQNKALPENVKYGIVLDAGSSHTSLYIYKWPAEKENDTGVVHQVEECRVK

GPGISKFVQKVNEIGIYLTDCMERAREVIPRSQHQETPVYLGATAGMRLL

RMESEELADRVLDVVERSLSNYPFDFQGARIITGQEEGAYGWITINYLLG

KFSQKTRWFSIVPYETNNQETFGALDLGGASTQVTFVPQNQTIESPDNAL

QFRLYGKDYNVYTHSFLCYGKDQALWQKLAKDIQVASNEILRDPCFHPGY

KKVVNVSDLYKTPCTKRFEMTLPFQQFEIQGIGNYQQCHQSILELFNTSY

CPYSQCAFNGIFLPPLQGDFGAFSAFYFVMKFLNLTSEKVSQEKVTEMMK

KFCAQPWEEIKTSYAGVKEKYLSEYCFSGTYILSLLLQGYHFTADSWEHI

HFIGKIQGSDAGWTLGYMLNLTNMIPAEQPLSTPLSHST

The fusion protein of the present invention preferably contains an amino acid sequence of the second linker according to the following SEQ ID NO. 5.

SEQ ID NO: 5
GGGGSGGGGSGGGGS

The present invention further relates to fragments of the fusion protein of the present invention and to polynucleotides encoding fragments of the fusion protein of the present invention.

A preferred polynucleotide is shown in the following SEQ ID NO. 6:

```
SEQ ID NO.: 6
Polynucleotide sequence (without stop codon):
ATGGAAACCCCTGCTCAGCTGCTGTTCCTGCTGCTGCTGTGGCTGCCTGA

CACCACCGGCCAGTCCGGACCTCTGCCTAAGCCTTCCCTGCAGGCCCTGC

CTTCCTCCCTGGTGCCTCTGGAAAAGCCTGTGACCCTGAGGTGTCAGGGA

CCTCCTGGCGTGGACCTGTACCGGCTGGAAAAGCTGTCCTCCAGCAGATA

CCAGGACCAGGCCGTGCTGTTCATCCCTGCCATGAAGCGGTCCCTGGCCG

GCAGGTACAGGTGCTCCTACCAGAACGGCTCCCTGTGGTCTCTGCCTTCT

GACCAGCTGGAACTGGTGGCTACCGGCGTGTTCGCCAAGCCTTCTCTGTC

TGCCCAGCCTGGACCTGCTGTCTCCTCTGGAGGCGACGTGACACTGCAGT

GCCAGACCAGATACGGCTTCGATCAGTTCGCCCTGTACAAAGAGGGCGAC

CCTGCCCCTTACAAGAACCCTGAGCGGTGGTACAGGGCCTCCTTCCCTAT

CATCACCGTGACCGCCGCTCACTCCGGCACCTACCGGTGCTACAGCTTCT

CCTCCCGGGACCCTTACCTGTGGTCCGCCCCTAGCGACCCTCTCGAACTG

GTCGTCACCGGAACCTCCGTGACCCCTTCCAGGCTGCCTACCGAGCCTCC

TAGCTCCGTGGCCGAGTTCTCTGAGGCCACCGCCGAGCTGACCGTGTCCT

TCACCAACAAGGTGTTCACCACCGAGACATCCCGGTCCATCACCACCTCC

CCCAAAGAGTCCGACTCTCCTGCCGGCCCTGCTCGGCAGTACTACACCAA

GGGCAACGGCGGCAGAGTGGAGTGTCCTCCTTGCCCTGCCCCTCCTGTGG

CTGGCCCTTCCGTGTTCCTGTTCCCTCCAAAGCCTAAGGACACCCTGATG

ATCTCCCGGACCCCTGAAGTGACCTGCGTGGTGGTGGACGTGTCCCACGA

GGACCCTGAGGTGCAGTTCAATTGGTACGTGGACGGCGTGGAGGTGCACA

ACGCCAAGACCAAGCCTCGGGAGGAACAGTTCAACTCCACCTTCCGGGTG

GTGTCCGTGCTGACCGTGGTGCACCAGGACTGGCTGAACGGCAAAGAATA

CAAGTGCAAGGTGTCCAACAAGGGCCTGCCTGCCCCTATCGAAAAGACCA

TCAGCAAGACCAAGGGACAGCCTCGCGAGCCTCAGGTGTACACCCTGCCT

CCAAGCCGGGAGGAAATGACCAAGAACCAGGTGTCCCTGACCTGCCTGGT

CAAGGGCTTCTACCCTTCCGATATCGCCGTGGAGTGGGAGTCTAACGGCC

AGCCTGAGAACAACTACAAGACCACCCCTCCTATGCTGGACTCCGACGGC

TCCTTCTTCCTGTACTCCAAACTGACCGTGGACAAGTCCCGGTGGCAGCA

GGGCAACGTGTTCTCCTGCTCCGTGATGCACGAGGCCCTGCACAACCACT

ACACCCAGAAGTCCCTGTCCCTGTCTCCTGGCAAGGGTGGAGGCGGTTCA

GGCGGAGGTGGCAGCGGCGGTGGCGGATCGACCCAGAACAAGGCCCTGCC

TGAGAACGTGAAGTACGGCATCGTGCTGGATGCTGGCTCCTCCCACACCT

CCCTGTACATCTACAAGTGGCCTGCCGAGAAAGAAAACGACACCGGCGTG

GTGCACCAGGTGGAGGAATGCAGAGTGAAGGGCCCTGGCATCTCCAAGTT

CGTGCAGAAAGTGAACGAGATCGGCATCTACCTGACCGACTGCATGGAAC

GGGCCAGGGAAGTGATCCCTCGGTCCCAGCATCAGGAAACCCCCGTCTAC

CTGGGCGCTACCGCCGGCATGCGGCTGCTGCGGATGGAATCCGAGGAACT

GGCCGACAGGGTGCTGGACGTGGTGGAGCGGTCCCTGTCCAACTACCCAT

TCGACTTTCAGGGCGCCAGGATCATCACCGGCCAGGAAGAGGGCGCTTAC

GGCTGGATCACCATCAACTACCTGCTGGGCAAGTTCTCCCAGAAAACCCG

GTGGTTCTCCATCGTGCCCTACGAGACAAACAACCAGGAAACCTTCGGCG

CTCTGGATCTGGGCGGAGCCTCTACCCAGGTGACCTTCGTGCCTCAGAAC

CAGACCATCGAGTCCCCCGACAACGCCCTGCAGTTCCGGCTGTACGGCAA

GGACTACAACGTGTACACCCACAGCTTTCTGTGCTATGGCAAGGACCAGG

CCCTGTGGCAGAAGCTGGCCAAGGACATCCAGGTGGCCTCCAACGAGATC

CTGCGGGACCCTTGCTTCCACCCTGGCTACAAGAAAGTGGTGAACGTGTC

CGACCTGTACAAGACCCCTTGCACCAAGCGGTTCGAGATGACCCTGCCTT

TCCAGCAGTTCGAGATCCAGGGCATCGGCAACTACCAGCAGTGCCACCAG

TCCATCCTGGAACTGTTCAACACCAGCTACTGCCCTTACTCCCAGTGCGC

CTTCAACGGCATCTTCCTGCCCCCTCTGCAGGGCGACTTCGGCGCCTTCT

CCGCCTTCTACTTCGTGATGAAGTTCCTGAACCTGACCTCCGAGAAGGTG

TCCCAAGAAAAAGTGACCGAGATGATGAAGAAGTTCTGCGCCCAGCCTTG

GGAGGAAATCAAGACCTCCTACGCTGGCGTGAAAGAGAAGTACCTGTCCG

AGTACTGCTTCTCCGGCACCTACATCCTGTCTCTGCTGCTGCAGGGCTAC

CACTTCACCGCCGACTCTTGGGAGCACATCCACTTCATCGGCAAGATCCA

GGGAAGCGACGCCGGCTGGACCCTGGGCTACATGCTGAATCTGACCAACA

TGATCCCTGCCGAGCAGCCTCTGTCCACCCCTCTGTCCCACTCCACC
```

The present invention further provides polypeptides having one or more residues deleted from the N-terminus of the amino acid sequence of a fusion protein of the present invention or an amino acid of any of the GPVI proteins, CD39 proteins, Fc portion proteins corresponding to the GPVI portion, CD39 portion, and Fc portion contained in the fusion protein of the present invention.

The present invention further provides polypeptides having one or more residues deleted from the carboxy terminus of the amino acid sequence of a fusion protein of the present invention or an amino acid of any of the GPVI proteins, CD39 proteins, Fc portion proteins corresponding to the GPVI portion, CD39 portion, and Fc portion contained in the fusion protein of the present invention.

Moreover, any of the N- or C-terminal deletions can be combined to produce a N- and C-terminal deleted fusion protein of the present invention. Accordingly, the invention also provides polypeptides having one or more amino acids deleted from both the amino and the carboxyl termini.

Polynucleotides encoding any of the polypeptides are also encompassed by the invention.

Whether a particular polypeptide lacking N-terminal residues and/or carboxy terminal residues of a complete polypeptide retains such therapeutic activities can readily be determined by routine methods.

The present invention is also directed to fusion proteins containing polypeptides at least 75%, 80%, 85%, 90%, 95%, 96%, 97%, 98% or 99% identical to polypeptide sequence of SEQ ID NO: 1). In preferred embodiments, the application is directed to proteins comprising polypeptides at least 75%, 80%, 85%, 90%, 95%, 96%, 97%, 98% or 99% identical to reference polypeptides having the amino acid sequence of N- and C-terminal deletions as described above. Polynucleotides encoding these polypeptides are also encompassed by the invention.

Preferred polypeptide fragments of the invention are fragments comprising, or alternatively, consisting of, an amino acid sequence that displays therapeutic activity by selectively binding collagen and having ectonucleotidase activity.

The present invention is also directed to proteins which comprise an amino acid sequence which is at least 75%, 80%, 85%, 90%, 95%, 96%, 97%, 98%, 99% or 100%, identical to SEQ ID NO: 1, 2, 3, 4, or 5.

The present invention also provides polypeptides encoded by polynucleotides which hybridize to the complement of a nucleic acid molecule encoding a fusion protein of the invention under the following stringent hybridization conditions:

Hybridization to filter bound DNA in 6×Sodium chloride/Sodium citrate (SSC) at about 45 degrees Celsius, followed by one or more washes in 0.2×SSC, 0.1% SDS at about 50-65 degrees Celsius.

The present invention also provides polypeptides encoded polynucleotides which hybridize to the complement of a nucleic acid molecule encoding a fusion protein of the invention under the following highly stringent conditions:

Hybridization to filter bound DNA in 6× sodium chloride/Sodium citrate (SSC) at about 45 degrees Celsius, followed by one or more washes in 0.1×SSC, 0.2% SDS at about 68 degrees Celsius.

A polypeptide having an amino acid sequence at least, for example, 95% "identical" to a query amino acid sequence, means that the amino acid sequence of the subject polypeptide is identical to the query sequence except that the subject polypeptide sequence may include up to five amino acid alterations per each 100 amino acids of the query amino acid sequence such as up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

Sequence identity can be determined by using conventionally known computer programs. A method for global sequence alignment uses the FASTDB computer program based on the algorithm of Brutlag et al. (Comp. App. Biosci. 6:237-245 (1990)). Homology or identity at the nucleotide or amino acid sequence level may be determined by BLAST analysis using the algorithm employed by the programs blastp, blastn, blastx, tblastn and tblastx (Karlin et al., Proc. Natl. Acad. Sci. USA 87: 2264-2268 (1990) and Altschul, J. Mol. Evol. 36: 290-300 (1993)).

The polynucleotide variants of the invention may contain alterations in the coding regions, non-coding regions, or both. Polynucleotide variants can be produced for a variety of reasons such as to optimize codon expression for a particular host.

Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, polypeptide variants in which less than 50, less than 40, less than 30, less than 20, less than 10, or 5-50, 5-25, 5-10, 1-5, or 1-2 amino acids are substituted, deleted, or added in any combination are also preferred.

In a preferred embodiment, a polynucleotide of the invention which encodes the fusion protein of the present invention is optimized for expression in mammalian cells such as CHO cells.

Naturally occurring variants are "allelic variants," and refer to one of several alternate forms of a gene occupying a given locus on a chromosome of an organism. Allelic variants can vary at either the polynucleotide and/or polypeptide level and are included in the present invention. Alternatively, non-naturally occurring variants may be produced by mutagenesis techniques or by direct synthesis.

Using methods of protein engineering and recombinant DNA technology, variants may be generated to improve or alter the characteristics of the polypeptides of the present invention. Moreover, ample evidence demonstrates that variants often retain a biological activity similar to that of the naturally occurring protein.

The invention provides variants of fusion proteins that have a functional activity. Such variants include deletions, insertions, inversions, repeats, and substitutions selected according to general rules known in the art so as have little effect on activity. Polynucleotides encoding such variants are also encompassed by the invention.

In preferred embodiments, the variants of the invention have conservative substitutions, which are swaps within groups such as replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. The resulting mutant molecules can then be tested for functional activity. Amino acid changes are likely to be permissive at certain amino acid positions in the protein as follows. Most amino acid residues buried in the tertiary structure require nonpolar side chains, whereas few features of surface side chains are generally conserved. Tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) polypeptides containing substitutions of one or more of the non-conserved amino acid residues, where the substituted amino acid residues may or may not be one encoded by the genetic code, or (ii) polypeptides containing substitutions of one or more of the amino acid residues having a substituent group, or (iii) polypeptides which have been fused with or chemically conjugated to another compound, such as a compound to increase the stability and/or solubility of the polypeptide (for example, polyethylene glycol), (iv) polypeptide containing additional amino acids, such as, for example, an IgG Fc fusion region peptide. Polypeptide variants containing amino acid substitutions of charged amino acids with other charged or neutral amino acids may produce proteins with improved characteristics, such as less aggregation.

In specific embodiments, the fusion proteins of the invention comprise, or alternatively, consist of, fragments or variants of the amino acid sequence of SEQ ID No: 1, wherein the fragments or variants have 1-5, 5-10, 5-25, 5-50, 10-50 or 50-150, amino acid residue additions, substitutions, and/or deletions when compared to SEQ ID No: 1. In preferred embodiments, the amino acid substitutions are conservative. Nucleic acids encoding these polypeptides are also encompassed by the invention.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

The ability of a fusion protein of the invention to bind or compete with a reference protein for binding to ligands such as collagen, ADP or an antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, agglutination assays (e.g., gel agglutination assays, hemagglutination assays), in situ immunoassays (using colloidal gold, enzyme or radioisotope labels), western blots, precipitation reactions, complement fixation assays, immunofluorescence assays, protein A assays, and immunoelectrophoresis assays, etc.

The ability of the fusion protein of the present invention to multimerize, in particular to dimerize, or association with other components of the multimer can be assayed, for example, by reducing and non-reducing gel chromatography, protein affinity chromatography, and affinity blotting.

Assays for the ability of the fusion proteins of the present invention to (specifically) bind a specific protein or epitope may be performed in solution (e.g., Houghten, Bio/Techniques 13:412-421(1992)), on beads (e.g., Lam, Nature 354:82-84 (1991)), or on chips (e.g., Fodor, Nature 364: 555-556 (1993)).

Immunoassays which can be used to analyze (immunospecific) binding and cross-reactivity include competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, (Ausubel et al, eds, 1994, Current Protocols in Molecular Biology, Vol. 1, John Wiley & Sons, Inc., New York, which is incorporated by reference herein in its entirety).

The Extracellular Domain of Glycoprotein VI (GPVI)

A fusion protein of the invention comprises an extracellular domain of glycoprotein VI, or a fragment or variant thereof, which is associated with the other portions of the fusion protein by genetic fusion.

The term "extracellular domain of glycoprotein VI" refers collectively to GPVI protein or amino acid sequence, or a GPVI fragment or variant, which selectively bind collagen. In particular, "extracellular domain of glycoprotein VI" refers to human extracellular domain of glycoprotein VI or fragments thereof (see for example, EP1511770) especially the mature form of human extracellular domain of glycoprotein VI as shown in SEQ ID NO: 2, or GPVI from other vertebrates or fragments thereof, or analogs or variants of these molecules or fragments thereof. Preferably, the first linker linking the extracellular domain of glycoprotein VI is linked to the Fc portion is a short linker having 2 to 8 amino acids, in particular a GGR linker.

The Fc Portion

A fusion protein of the invention comprises an Fc portion, or a fragment or variant thereof, which is associated with the other portions of the fusion protein by genetic fusion.

The term "Fc portion" refers collectively to the Fc portion of IgG1 or IgG2 protein or amino acid sequence, or an Fc portion fragment or variant, which is able to dimerize. In particular, "Fc" refers to human Fc portions or fragments thereof (see for example, EP1511770). Preferably, the Fc portion includes a partial hinge region, and the CH2 and CH3 domain of human IgG1 or IgG2, especially an Fc portion derived from IgG as shown in SEQ ID NO: 3, or Fc portions from other vertebrates or fragments thereof, or analogs or variants of these molecules or fragments thereof.

The Extracellular Domain of CD39 Protein (CD39)

A fusion protein of the invention comprises, furthermore, an extracellular domain of a CD39 protein, or a fragment or variant thereof, which is associated with the other portions of the fusion protein by genetic fusion.

The term "extracellular domain of CD39 protein" refers collectively to CD39 protein or amino acid sequence, or a CD39 fragment or variant, which have ectonucleotidase activity. In particular, "extracellular domain of CD39" refers to human CD39 protein or fragments thereof especially the mature form of a human extracellular domain of CD 39 as shown in SEQ ID NO: 4, or from other vertebrates or fragments thereof, or analogs or variants of these molecules or fragments thereof.

Preferred fusion proteins of the invention are fusion proteins encoded by a nucleic acid molecule comprising, or alternatively consisting of, a polynucleotide encoding at least one molecule of the extracellular domain of GPVI (or a fragment or variant thereof) joined in frame via a first linker sequence to at least one polynucleotide encoding at least one molecule of an Fc portion (or fragment or variant thereof) joined in frame via a second linker sequence to a polynucleotide encoding at least one molecule of the extracellular domain of CD39 (or a fragment or variant thereof).

Preparation of the Fusion Proteins of the Present Invention

The fusion proteins of the invention may be produced as recombinant molecules by secretion from a mammalian cell line, yeast, or a microorganism such as a bacterium. Preferably, the polypeptide is secreted from the host cells.

A particular embodiment of the invention comprises a DNA construct encoding a signal sequence effective for directing secretion in a host cell such as a mammalian host cell, particularly a signal sequence of SEQ ID No: 7, and the fusion protein of the invention without any further sequence between the signal and the mature polypeptide.

SEQ ID NO: 7
METPAQLLFLLLLWLPDTTG

The above signal is a preferred example of a mammalian cell derived signal sequence.

The present invention also relates to a cell line, preferably a mammalian cell line transformed to express a fusion protein of the invention. In addition to the transformed host cell lines, the present invention also relates to a culture of those cells, preferably a monoclonal culture, or a culture derived from a monoclonal culture, in a nutrient medium, wherein the secreted polypeptide is contained in the medium with the cells, or without the cells.

A representative clone CHO GPVI-Fc-linker-CD39 containing a fusion construct of the invention was deposited with the Leibniz-Institut DSMZ-Deutsche Sammlung von Microorganismen and Zellkulturen on Jun. 29, 2017 under DSMZ under Accession Number DSM ACC3322 (identification reference CHO GPVI-Fc-linker-CD39). The DSMZ is located at Inhoffenstraße 7 B, 38124 Braunschweig, Germany. The DSMZ deposits were made pursuant to the terms of the Budapest Treaty on the international recognition of the deposit of microorganisms for the purposes of patent procedure.

Many expression systems are known and may be used, including mammalian cells such as CHO cell, bacterial cells (for example *E. coli* and *Bacillus subtilis*), yeasts (for example *Saccharomyces cerevisiae*), filamentous fungi (for example *Aspergillus*), plant cells, animal cells and insect cells. Flp-In™-CHO cells (Life Technologies, Carlsbad, Calif.) which had been genetically modified to harbor the cDNA for a Tet repressor protein, are preferred.

The fusion protein of the present invention is produced in conventional ways, for example from a coding sequence inserted in the host chromosome or on a free plasmid. The cells are transformed with a coding sequence for the desired protein in any of the usual ways.

Useful fusion constructs are vectors which are generally available e.g. from Life Technologies, Carlsbad, Calif. A mammalian expression vector pcDNA5/FRT/TO is particularly preferred.

Preferably, Flp-In™-CHO cells are stably transfected with a fusion construct and pOG44 helper plasmid using a transfection reagent. A suitable transfection reagent is Lipofectamine®, including Lipofectamine 2000®.

Successfully transformed cells, i.e., cells that contain a DNA construct of the present invention, can be identified by conventional techniques. For example, cells resulting from the introduction of an expression construct can be grown to produce the desired polypeptide. Preferably, stable adherent cells are adapted to growth in suspension in a chemically defined growth medium. In case of mammalian expression vector pcDNA5/FRT/TO, recombinant protein expression may be induced by addition of Doxycycline followed by incubation in a humidified atmosphere.

Cells can be harvested and lysed and their DNA content examined for the presence of the DNA using a method such as that described by Southern (1975) J. Mol Biol. 98, 503 or Berent et al. (1985) Biotech. 3, 208. Alternatively, the presence of the protein in the supernatant can be detected using antibodies. The presence and quantity of fusion proteins of the invention may be determined using ELISA comprising the steps of coating an ELISA plate with an anti-human serum antibody, blocking the plate to prevent non-specific binding, washing the ELISA plate, adding a solution containing the fusion protein of the invention, adding a secondary anti-fusion protein specific antibody coupled to a detectable label, and detecting the presence of the secondary antibody.

Fusion proteins of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. Preferably, the fusion proteins of the invention are purified using Affinity Chromatography including peptide affinity and antibody affinity columns that are selective for the fusion protein molecules of the present invention.

Most preferably, high performance affinity chromatography using a protein G sepharose column and their equivalents and comparables is employed for purification.

Fusion proteins of the present invention may be recovered from: products produced by recombinant techniques from mammalian cells, a prokaryotic or eukaryotic host or products of chemical synthetic procedures. Depending upon the host employed in a recombinant production procedure, the polypeptides of the present invention may be glycosylated or may be non-glycosylated.

In addition, fusion proteins of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide can be synthesized by use of a peptide synthesizer.

Furthermore, if desired, nonclassical amino acids or chemical amino acid analogs can be introduced as a substitution or addition into the polypeptide sequence. Non-classical amino acids include the D-isomers of the common amino acids, a-amino isobutyric acid, 2,4-diaminobutyric acid, 4-aminobutyric acid, 2-amino butyric acid, g-Abu, e-Ahx, Aib, 6-amino hexanoic acid, 2-amino isobutyric acid, 3-amino propionic acid, ornithine, norleucine, norvaline, hydroxyproline, sarcosine, citrulline, homocitrulline, t-butylglycine, t-butylalanine, phenylglycine, cyclohexylalanine, cysteic acid, b-alanine, fluoro-amino acids, and amino acid analogs in general.

The fusion proteins may also be modified with a detectable label, such as an enzymatic, fluorescent, isotopic or affinity label to allow for detection and isolation of the protein.

The fusion proteins of the invention may be modified by either natural processes, such as post-translational processing, or by chemical modification techniques which are well known in the art. It will be appreciated that the same type of modification may be present in the same or varying degrees at several sites in a given polypeptide.

Chemically modified derivatives of the fusion proteins of the invention may provide additional advantages such as increased solubility, stability and circulating time of the polypeptide, or decreased immunogenicity. The chemical moieties for derivatization may be selected from water soluble polymers such as polyethylene glycol, ethylene glycol/propylene glycol copolymers, carboxymethylcellulose, dextran, polyvinyl alcohol and the like. The fusion proteins may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa for ease in handling and manufacturing. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

The fusion proteins of the invention or formulations thereof may be administered by any conventional method including parenteral infusion. The term "parenteral" refers to modes of administration which include intravenous, intramuscular, intraperitoneal, subcutaneous and intraarticular injection and infusion.

The treatment may consist of a single dose or a plurality of doses over a period of time.

While it is possible for a fusion protein of the invention to be administered alone, it is preferable to present it as a pharmaceutical formulation, together with one or more acceptable carriers compatible with the fusion protein and not deleterious to the recipients thereof. Typically, the carriers will be sterile and pyrogen free water or saline. The formulations of the invention are typically non-immunogenic, in part, because of the use of the components of the fusion protein being derived from the proper species. For instance, for human use, the GPVI portion and the CD39 portion will typically be human. In some cases, wherein either component is non human-derived, that component may be humanized by substitution of key amino acids so that specific epitopes appear to the human immune system to be human in nature rather than foreign.

The formulations may be presented in unit dosage form and may be prepared by any of the methods well known in the art of pharmacy. Such methods include the step of bringing into association the fusion protein with the carrier that constitutes one or more accessory ingredients. In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain antioxidants, buffers, bacteriostats and solutes which render the formulation appropriate for the intended recipient as well as aqueous and non-aqueous sterile suspensions which may include suspending agents and thickening agents. The formulations may be presented in unit-dose or multi-dose containers, for example sealed ampules, vials or syringes, and may be stored in a freeze-dried (lyophilised) condition requiring only the addition of the sterile liquid carrier, for example water for injections, immediately prior to use. Extemporaneous injection solutions and suspensions may be prepared from sterile powders.

The invention also provides methods of treatment and/or prevention of diseases or disorders by administration to a subject of an effective amount of a fusion protein of the invention in a pharmaceutically acceptable carrier. The fusion protein will be formulated and dosed in a fashion consistent with good medical practice, taking into account the clinical condition of the individual patient, the site of delivery, the method of administration, the scheduling of administration, and other factors known to practitioners. The "effective amount" for purposes herein is thus determined by such considerations. As a general proposition, the total pharmaceutically effective amount of the fusion protein administered parenterally per dose will be in the range of about 1 ug/kg/day to 10 mg/kg/day of patient body weight, although, as noted above, this will be subject to therapeutic discretion.

For parenteral administration, in one embodiment, the fusion protein is formulated generally by mixing it at the desired degree of purity, in a unit dosage injectable form, with a pharmaceutically acceptable carrier, i.e., one that is non-toxic to recipients at the dosages and concentrations employed and is compatible with other ingredients of the formulation.

Generally, the formulations are prepared by contacting the fusion protein and/or polynucleotide uniformly and intimately with liquid carriers or finely divided solid carriers or both. Then, if necessary, the product is shaped into the desired formulation. Preferably, the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates (including, for example, Tween-20), poloxamers, or PEG.

The fusion protein is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

The invention also provides a pharmaceutical pack or kit comprising one or more containers filled with one or more of the ingredients of the fusion proteins of the invention. Associated with such container can be a notice in the form prescribed by a governmental agency regulating the manufacture, use or sale of pharmaceuticals or biological products, which notice reflects approval by the agency of manufacture, use or sale for human administration.

EXAMPLES

Methods

Reageants and Antibodies

Standard laboratory chemicals were purchased from Carl Roth (Karlsruhe, Germany). Hams' F-12 growth medium, fetal bovine serum, PBS, and glutamine were from Biochrom (Berlin, Germany). Blasticidin S was obtained from InvivoGen (San Diego, Calif.). Hygromycin B came from Carl Roth (Karlsruhe, Germany). ProCHO4 growth medium was from LONZA (Basel, Switzerland). All enzymes for cloning were bought from New England Biolabs (Frankfurt, Germany). Doxycycline hydrochloride, Adenosine 5'-diphosphate (ADP) sodium salt, and Adenosine 5'-triphosphate (ATP) disodium salt hydrate were purchased from Sigma Aldrich (Munich, Germany). A part of the recombinant hirudin was a kind gift from Prof. Sommerhoff (University of Munich), another part was purchased from Celgene (Summit, N.J.). Collagen-related peptide (CRP) was synthetized at AnaSpec (Fremont, Calif.) and chemically cross linked to gain CRP-XL. DiOC6 was from Life Technologies (Eugene, Oreg.). Midazolam (Dormicum®) was purchased from Roche (Basel, Switzerland), Medetomidin (Dormitor®) and Fentanyl were both from Janssen-Cilag (Neuss, Germany). Recombinant soluble human CD39 (solCD39) was obtained from R&D Systems (Minneapolis, Minn.). Goat-anti-human Fcγ and goat-anti-human IgG (H+L)-POD were purchased from Jackson ImmunoResearch (West Baltimore Pike, Pa.).

Cloning and Protein Production

GPVI-Fc (Revacept) was taken from existing stocks. The cDNA coding for the fusion protein consisting of the extracellular domain of platelet glycoprotein VI, Fc (partial hinge region, CH2 and CH3 domain) of human IgG2 and the extracellular domain of human CD39 which was connected by a 15 amino acid linker (GPVI-CD39) was established by gene synthesis (Life Technologies, Carlsbad, Calif.). For steric reasons, the sequence coding for the Fc part of human IgG2 was inserted into the GPVI-CD39 fusion protein, whereas the original GPVI-Fc (also termed Revacept, which is currently in clinical investigation) is composed of the Fc derived from human IgG1. The cDNA was cloned into the mammalian expression vector pcDNA5/FRT/TO (Life Technologies, Carlsbad, Calif.) using HindIII and BamHI sites. Flp-In™-CHO cells (Life Technologies, Carlsbad, Calif.) which had been genetically modified to harbor the cDNA for a Tet repressor protein were stably transfected with the expression construct and pOG44 helper plasmid using Lipofectamine 2000 transfection reagent according to the instructions of the supplier (both Life Technologies, Carlsbad, Calif.). Stable adherent cells were adapted to growth in suspension in the chemically defined growth medium ProCHO4 supplemented with 4 mM glutamine, 600 µg/ml Hygromycin B, and 20 µg/ml Blasticidin S. Recombinant protein expression was induced in dense cultures by addition of 30 ng/ml Doxycycline followed by incubation at 31° C. and 5% $CO_2$ for 6-7 d in a humidified atmosphere. The construct for the control protein was produced by gene synthesis, accordingly. Expression of Fc(IgG2) control proteins was performed in stably transfected Flp-In™-CHO cells grown at 37° C., 5% CO2 for 3-4 d in Ham's F-12 medium with 2% fetal bovine serum which had been depleted for bovine IgG in advance. Recombinant proteins were purified from cell culture supernatants using HiTrap Protein G HP affinity chromatography columns (VWR, Darmstadt, Germany) according to the manufacturer's manual. All proteins were dialyzed against phosphate-buffered saline (PBS). Purified GPVI-CD39 protein was separated in non-reducing and reducing sample buffer on a Tris-Hepes NH 4-20% gradient gel (NuSep, Bogart, Ga.) which was stained with Coomassie Brilliant Blue G250.

ADPase Activity

Various concentrations of GPVI-CD39 or solCD39 protein or plasma samples from the pharmacokinetic study diluted 1:500-1:2000 in assay buffer were incubated in 25 mM Tris-HCl, 5 mM $CaCl_2$, pH 7.5 with 200 µM ADP in a total volume of 100 µl for 30 min or 5 min at 37° C. Enzymatically released Pi was detected using the Malachite Green Phosphate Detection Kit (R&D Systems, Minneapolis, Minn.) according to the supplier's manual. A serial dilution of Pi standard was analyzed in parallel which facilitates quantification of released Pi. Absorbance was measured at a wave length of 630 nm using a Tecan Infinite 200 ELISA reader. Enzymatic activity of purified protein was calculated taking incubation time and protein amount into account and expressed as Units per mg of protein.

Blood Collection

Blood was withdrawn from healthy volunteers that did not take any anti-coagulative medication within the last 14 days, with either recombinant hirudin (200 U/ml; 13 µg/ml) or citrate as anti-coagulant. Informed consent was obtained as approved by the local Ethics Committee. An overall number of 58 healthy volunteers was included into the study: blood samples from 39 subjects were taken for in vitro experiments using vascular agonists, and blood samples from 19 subjects for experiments involving human plaque material.

Platelet Aggregation

The effect of GPVI-CD39 and control proteins on platelet aggregation was analyzed using the Multiplate® device (25). 1:1 diluted hirudin-anticoagulated blood was preincubated with antagonist for 3 min in the test cell without stirring to avoid platelet pre-activation (26). Agonist was added and samples were incubated for 6 min at 37° C. with stirring. The following agonists were used: 6.5 µM ADP, 12 µg/ml collagen isolated from rabbit aorta, or 103 µg/ml collagen type I secreted by human fibroblasts (VitroCol®, Advanced BioMatrix, San Diego, Calif.). Platelet aggregation was measured in arbitrary units over the time period (arbitrary units (AU)*min) (cumulative aggregation values).

In Vivo Thrombus Formation after $FeCl_3$ Injury in Carotid Arteries

For examination of arterial thrombus formation in vivo, 6-8 weeks old C57BL/6J wild type mice were anesthetized by injection of midazolame (5 mg/kg body weight), medetomidine (0.5 mg/kg body weight) and fentanyl (0.05 mg/kg body weight). In the ferric chloride model, an overall number of 21 mice was studied.

The common carotid artery was dissected free and the mice were injected intravenously 30 minutes before carotid injury with GPVI-CD39 (3 mg/kg body weight) or its control and with GP1bα-488 (Emfret Analytics, Eibelstadt, Germany) for platelet visualization. The carotid was exteriorized and injured by topical application of a filter paper saturated with 15% ferric chloride for 1 minute. Thrombus formation in arteries was monitored for 20 minutes or until complete occlusion (stop of blood flow for >1 min). Digital films and images were recorded with a Nikon eclipse intravital microscope and analysed offline.

Pharmacokinetic Analysis ale and female wild type C57BL/6J mice of the age of 12-22 weeks were used in this small scale study. An overall number of 9 mice were investigated. GPVI-CD39 or solCD39 were applied in a volume of 5 ml/kg into the right tail vein. At time points indicated in the figure blood sampling was performed by incision of the left tail vein using 25 µl heparinized capillaries. Blood samples were recovered by centrifugation at 2400×g for 10 min. The upper plasma phase was transferred to fresh tubes and stored frozen at −20° C.

Determination of Protein Concentration in Plasma Samples of Mice

The concentration of GPVI-CD39 or Fc control protein in plasma samples was determined by Fc-specific sandwich ELISA. Wells of a MaxiSorp 96-well plate (Thermo Fisher Scientific, Waltham, Mass.) were coated with 0.1 µg/well goat-anti-human Fcγ antibody. Wells were washed three times with phosphate-buffered saline and tween-20 (PBST) between incubations. After blocking with 3% skimmed milk in PBST wells were incubated for 1 h with 50 µl of plasma from GPVI-CD39 treated (1:200) or Fc (1:500) treated mice diluted in PBST. Wells were incubated for 1 h with 100 µl of 80 ng/ml goat-anti-human IgG (H+L)-POD detection antibody. POD activity was visualized using 100 µl of Ultra TMB-ELISA substrate (Thermo Fisher Scientific, Waltham, Mass.) and signal intensities were read with a Tecan Infinite F200 ELISA reader.

Analysis of In Vivo Tail Bleeding Time in Mice

Test or control substances were applied into the tail vein of C57BL/6J mice. Animals were anesthetized by intraperitoneal injection of 0.5 mg/kg medetomidine, 5 mg/kg midazolame, and 0.05 mg/kg fentanyl. 10 min after protein delivery a blood sample of 20 µl was drawn for analysis of recombinant protein content and ADPase activity using a heparinized capillary. 15 min after protein application the distal 2 mm of the tail were cut off, the tail was immediately immersed into pre-warmed PBS (37° C.) buffer and time-monitored until bleeding stopped for at least 30 s. The process was standardized to yield comparable results over time and results were reproducible. Animals were sacrificed and a final blood sample stored for analysis.

Determination of In Vitro Closure Time with Innovance® PFA-200 (Siemens Healthcare Diagnostics)

Citrated blood of healthy donors was mixed with antagonist in concentrations indicated in the figures, and added to Dade® PFA COL/EPI, Dade® PFA COL/ADP, or Innovance® PFA P2Y test cartridges (Siemens Healthcare, Erlangen, Germany). Blood was aspirated under high shear conditions (>5000/s) through a capillary onto a membrane with a small aperture coated with substances which activate platelets and lead to closure of this aperture. The time until closure of this aperture is monitored and expressed as in vitro closure time with a maximum closure time of 300 s.

Statistics

Normal distribution of all analysed parameters was verified and confirmed by Kolmogorov-Smirnov testing. Differences between two or more experimental groups were analyzed by ANOVA using SPSS software (version 19), followed by Fisher's LSD (least significant difference) post-hoc testing. Specifically, 2-way-repeated measures ANOVA was used where indicated. Student's t-test Bonferroni's method was additionally used when absence of differences in ADPase activity was investigated.

Results

Description of GPVI-CD39 Protein and its Properties

Figure 1:
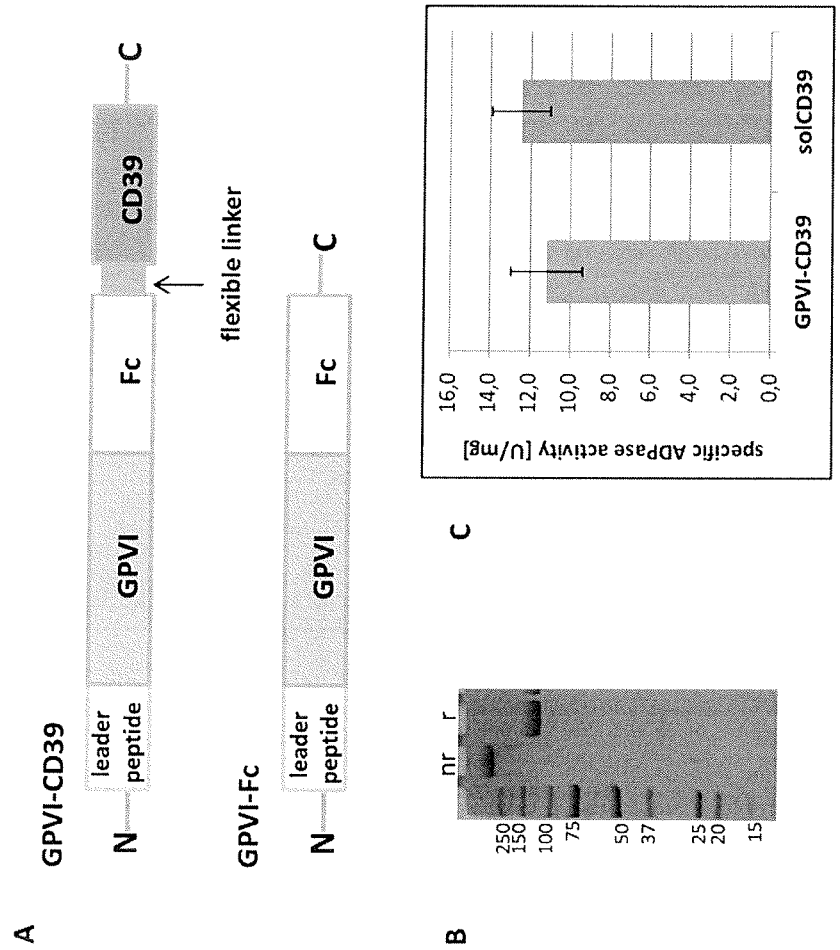
FIG. 1 shows a structure scheme and biochemical characterization of bifunctional, recombinant GPVI-CD39 compared to GPVI-Fc.

To enhance the anti-thrombotic potential of Revacept (GPVI-Fc), we created a fusion protein which combines the extracellular collagen binding domain of GPVI with the extracellular domain of CD39 harbouring enzymatic ADPase activity (FIG. 1A). The Fc-domain in between facilitates dimerisation of the molecule as was confirmed by non-reducing polyacrylamide gel analysis (FIG. 1B). A flexible linker of 15 amino acids facilitates proper folding of the CD39 domain. The protein was successfully expressed by doxycycline-inducible stably transfected CHO cells and was purified from cellular supernatants by Protein G affinity chromatography. At various concentrations, the fusion protein exhibited a mean ADPase activity of 11.2±4.0 U/mg which was similar to that of commercially available soluble CD39 (solCD39, 12.5±3 U/mg) (28). These results are shown in FIG. 1 C. Statistical comparison of GPVI-CD39 with solCD39 activities (equal amounts) yielded no significant difference by either t testing or ANOVA.

Effect of GPVI-Fusion Proteins on Collagen-, ADP- or Plaque-Induced Platelet Aggregation in Human Blood Under Static Conditions The effect of GPVI-CD39 on collagen induced aggregation of human platelets was analyzed in blood using collagens from different sources as well as human plaque material and the secondary agonist ADP. GPVI-CD39 exhibited a highly significant, dose-dependent inhibition of platelet aggregation induced by 12 µg/ml collagen isolated from rabbit aorta (FIG. 2A). Similarly, using 103 µg/ml collagen secreted by human fibroblasts (VitroCol®, mainly type I collagen) as agonist, GPVI-CD39 inhibited platelet aggregation significantly whereas GPVI-Fc only resulted in a minor inhibition at the same concentration (FIG. 2B). Effective inhibition of ADP-induced platelet aggregation occurred by GPVI-CD39 as well as by equimolar concentrations of solCD39, using 6.5 µM ADP, whereas GPVI-Fc lacking the CD39 component displayed no inhibitory effect (FIG. 2C). Adding GPVI-CD39 to platelet aggregation triggered by human plaque material (333 µg/ml) also resulted in a dose-dependent inhibition with an approximate $IC_{50}$-value of 30 nmol/L (FIG. 3). GPVI-Fc tested at the same concentrations was markedly and significantly less effective than GPVI-CD39.

Anti-thrombotic Effects of GPVI-CD39 In Vivo in a $FeCl_3$-Model

To investigate the anti-thrombotic effects of GPVI-CD39 in vivo in mice the common carotid artery was injured using 15% ferric chloride and the time to occlusion of the vessel was monitored. In wild type mice the mean time to vessel occlusion was 480 s (not shown). IV administration of either vehicle (NaCl) or of 1.5 mg/kg (10 nmol/kg) GPVI-Fc resulted in similar occlusion times, whereas 3 mg/kg (10 nmol/kg) GPVI-CD39 significantly delayed vessel occlusion to 1083 s (FIG. 5).

Assessment of Closure Times by PFA-200

The efficacy of GPVI-CD39 was also analyzed by measuring closure times in response to various agonists with a platelet function analyzer (Innovance® PFA-200). Four different concentrations of GPVI-CD39 were tested ranging from 21.7 to 217 nmol/L. Using either COL/ADP or COL/EPI cartridges, no significant increase of closure times of the aperture compared to the buffer control (phosphate-buffered saline—PBS) was observed (FIGS. 6A and B). Using the COL/EPI cartridges, only acetyl salicylic acid (ASA), used as a positive control, inhibited the closure of the aperture completely over the analyzed time period. As expected, P2Y cartridges which allow for sensitive detection of P2Y antagonism showed a statistically significant increase in closure time using 47 and 217 nmol/L GPVI-CD39, but not with 21 nmol/L (FIG. 6C). The prolongations with higher concentrations of GPVI-CD39 corresponded to those observed with 1.9 μM of the $P2Y_{12}$ inhibitor ticagrelor (FIG. 6C). These results thus confirmed the effective inhibition of the secondary agonist ADP by GPVI-CD39.

Pharmacokinetic Analysis and In Vivo Bleeding Time Determination in Mice

Since the application of effective doses of solCD39 in various animal models of thrombosis caused higher bleeding risks, the hazard potential of GPVI-CD39 was analyzed by measuring in vivo bleeding times in mice. In order to determine a proper time point after protein application for an in vivo bleeding study, a pharmacokinetic study of GPVI-CD39 plasma concentrations was performed. Mice were injected with 4 mg/kg of GPVI-CD39 or 2 mg/kg solCD39—these doses relate to 26.6 nmol of the CD39 moieties of both agents.

Blood sampling was performed at intervals indicated in FIG. 7 A and both the content of Fc-containing protein (GPVI-CD39) and ADPase activity in plasma were determined. 5 min after protein application a mean concentration of GPVI-CD39 of 95 μg/ml was detected. solCD39 could not be analyzed because of the lack of an Fc-portion. Concentration of the protein decreased rapidly in the course of two hours. After 48 h, GPVI-CD39 was still detectable at a low concentration of 6 μg/ml.

ADPase activity was measured in the same plasma samples for solCD39, and comparable to that of GPVI-CD39 (FIG. 7 B). ADPase activity diminished rapidly during the first 60 min but was still detectable at very low levels after 2 d.

The analysis of tail bleeding time 15 min after IV administration showed no differences for 4 mg/kg (13 nmol/kg) GPVI-CD39 compared to 2 mg/kg (13 nmol/kg) GPVI-Fc or vehicle or buffer controls (FIG. 7 C).

REFERENCES

1. Mackay J, Mensah G. The Atlas of heart disease and stroke. World Health Organisation 30-9-2004.
2. Marsh J D, Keyrouz S G. Stroke Prevention and Treatment. J Am Coll Cardiol 2010; 56: 683-691.
3. Stoll G, Kleinschnitz C, Nieswandt B. The role of glycoprotein Ibalpha and von Willebrand factor interaction in stroke development. Hamost 2010; 30: 136-138.
4. Penz S, Reininger A J, Brandl R, Goyal P, Rabie T, Bernlochner I, Rother E, Goetz C, Engelmann B, Smethurst P A, Ouwehand W H, Farndale R, Nieswandt B, Siess W. Human atheromatous plaques stimulate thrombus formation by activating platelet glycoprotein VI. Faseb J 2005; 19(8):898-909.
5. Reininger A J, Bernlochner I, Penz S M, Ravanat C, Smethurst P, Farndale R W, Gachet C, Brandl R, Siess W. A 2-step mechanism of arterial thrombus formation induced by human atherosclerotic plaques. J Am Coll Cardiol 2010; 55:1147-58.
6. Schulz C, Penz S, Hoffmann C, Langer H, Gillitzer A, Schneider S, Brandl R, Seidl S, Massberg S, Pichler B, Kremmer E, Stellos K, Schonberger T, Siess W, Gawaz M. Platelet GPVI binds to collagenous structures in the core region of human atheromatous plaque and is critical for atheroprogression in vivo. Basic Res Cardiol 2008; 103:356-67.
7. Jandrot-Perrus M, Busfield S, Lagrue A H, Xiong X, Debili N, Chickering T, Le Couedic J P, Goodearl A, Dussault B, Fraser C, Vainchenker W, Villeval J L. Cloning, characterization, and functional studies of human and mouse glycoprotein VI: a platelet-specific collagen receptor from the immunoglobulin superfamily. Blood 2000; 96:1798-1807
8. Zahid M, Mangin P, Loyau S, Hechler B, Billiald P, Gachet C, Jandrot-Perrus M. The future of glycoprotein VI as an antithrombotic target. J Thromb Haemost 2012; 10:2418-27.
9. Massberg S, Konrad I, Bültmann A, Schulz C, Münch G, Peluso M, Lorenz M, Schneider S, Besta F, Müller I, Hu B, Langer H, Kremmer E, Rudelius M, Heinzmann U, Ungerer M, Gawaz M. Soluble glycoprotein VI dimer inhibits platelet adhesion and aggregation to the injured vessel wall in vivo. Faseb J 2004; 18:397-9.
10. Ungerer M, Rosport K, Bultmann A, Piechatzek R, Uhland K, Schlieper P, Gawaz M, Munch G. Novel antiplatelet drug revacept (dimeric glycoprotein VI-Fc) specifically and efficiently inhibited collagen-induced platelet aggregation without affecting general hemostasis in humans. Circulation 2011; 123:1891-1899.
11. Dutting S, Bender M, Nieswandt B. Platelet GPVI: a target for antithrombotic therapy?! Trends Pharmacol Sci 2012; 33:583-590.
12. Jamasbi J, Megens R T, Bianchini M, Münch G, Ungerer M, Faussner A, Sherman S, Walker A, Goyal P, Jung S, Brandl R, Weber C, Lorenz R, Farndale R, Elia N, Siess W. Differential inhibition of human atherosclerotic plaque-induced platelet activation by dimeric GPVI-Fc and anti-GPVI antibodies: Functional and imaging studies. J Am Coll Cardiol 2015; 65:2404-2415
13. Arthur J F, Dunkley S, Andrews R K. Platelet glycoprotein VI-related clinical defects. Brit J Haematol 2007; 139:363-372
14. Eikelboom J W, Hirsh J, Spencer F A, Baglin T P, Weitz J I. Antiplatelet drugs: antithrombotic therapy and prevention of thrombosis. American College of Chest Physicians Evidence-Based Clinical Practice Guidelines. Chest 2012; 141(2 suppl):e89S-e119S
15. Ungerer M, Münch G. Novel antiplatelet drugs in clinical development. Thromb Haemost, 2013; 110:868-75.

16. Birk A V, Broekman M J, Gladek E M, Robertson H D, Drosopoulos J H, Marcus A J, Szeto H H. Role of extracellular ATP metabolism in regulation of platelet reactivity. J Lab Clin Med 2002; 140:166-175.
17. Marcus A J, Broekman M J, Drosopoulos J H, Islam N, Alyonycheva T N, Safier L B, Hajjar K A, Posnett D N, Schoenborn M A, Schooley K A, Gayle R B, Maliszewski C R. The endothelial cell ecto-ADPase responsible for inhibition of platelet function is CD39. J Clin Invest 1997; 99: 1351-1360
18. Marcus A J, Broekman M J, Drosopoulos J H, Olson K E, Islam N, Pinsky D J, Levi R. Role of CD39 (NTPDase-1) in thromboregulation, cerebroprotection, and cardioprotection. Semin Thromb Hemost 2005; 2: 234-246
19. Penz S M, Reininger A J, Toth O, Deckmyn H, Brandl R, Siess W. Glycoprotein Ibalpha inhibition and ADP receptor antagonists, but not aspirin, reduce platelet thrombus formation in flowing blood exposed to atherosclerotic plaques. Thromb Haemost 2007; 97: 435-443.
20. Gayle R B III, Maliszewski C R, Gimpel S D, Schoenborn M A, Caspary R G, Richards C, Brasel K, Price V, Drosopoulos J H, Islam N, Alyonycheva T N, Broekman M J, Marcus A J. Inhibition of platelet function by recombinant soluble ecto-ADPase/CD39. J Clin Invest 1998; 101:1851-1859.
21. Buergler J M, Maliszewski C R, Broekman M J, Kaluza G L, Schulz D G, Marcus A J, Raizner A E, Kleiman N S, Ali N M. Effects of SolCD39, a novel inhibitor of Platelet Aggregation, on Platelet Deposition and Aggregation after PTCA in a Porcine Model. J Thromb Thrombolysis 2005; 19:115-122
22. Dwyer K M, Robson S C, Nandurkar H H, Campbell D J, Gock H, Murray-Segal L J, Fisicaro N, Mysore T B, Kaczmarek E, Cowan P J, d'Apice A J. Thromboregulatory manifestations in human CD39 transgenic mice and the implications for thrombotic disease and transplantation. J Clin Invest. 2004; 113:1440-1446.
23. Hohmann J D, Wang X, Krajewski S, Selan C, Haller C A, Straub A, Chaikof E L, Nandurkar H H, Hagemeyer C E, Peter K H. Delayed targeting of CD39 to activated platelet GPIIb/IIIa via a single-chain antibody: breaking the link between antithrombotic potency and bleeding? Blood 2013; 121: 3067-3075
24. Brandl R., Richter T, Haug K, Wilhelm M G, Maurer P C, Nathrath W. Topographic analysis of proliferative activity in carotid endarterectomy specimens by immunocytochemical detection of the cell cycle-related antigen Ki-67. Circulation 1997; 96: 3360-3368
25. Toth O, Calatzis A, Penz S, Losonczy H, Siess W. Multiple electrode aggregometry: A new device to measure platelet aggregation in whole blood. Thromb Haemost 2006; 96:781-788
26. Bampalis V G, Brantl S A, Siess W. Why and how to eliminate spontaneous platelet aggregation in blood measured by multiple electrode aggregometry. J Thromb Haemost 2012; 10: 1710-1714
27. Liu, B. Tang D. Influence of non-Newtonian properties of blood on the wall shear stress in human atherosclerotic right coronary arteries. Mol Cell Biomech 2011; 8: 73-90
28. Huttinger Z M, Milks M W, Nickoli M S, Aurand W L, Long L C, Wheeler D G, Dwyer K M, d'Apice A J, Robson S C, Cowan P J, Gumina R J. Ectonucleotide triphosphate diphosphohydrolase-1 (CD39) mediates resistance to occlusive arterial thrombus formation after vascular injury in mice. Am J Pathol 2012; 181:322-333
29. Cai M, Huttinger Z M, He H, Zhang W, Li F, Goodman L A, Wheeler D G, Druhan L J, Zweier J L, Dwyer K M, He G, d'Apice A J, Robson S C, Cowan P J, Gumina R J. Transgenic over-expression of ectonucleotide triphosphate diphosphohydrolase-1 protects against murine myocardial ischemic injury. J Mol Cell Cardiol 2011; 51:927-935
30. Wheeler D G, Joseph M E, Mahamud S D, Aurand W L, Mohler P J, Pompili V J, Dwyer K M, Nottle M B, Harrison S J, d'Apice A J, Robson S C, Cowan P J, Gumina R J. Transgenic swine: expression of human CD39 protects against myocardial injury. J Mol Cell Cardiol. 2012; 52: 958-961
31. Pinsky D J, Broekman M J, Peschon J J, Stocking K L, Fujita T, Ramasamy R, Connolly E S Jr, Huang J, Kiss S, Zhang Y, Choudhri T F, McTaggart R A, Liao H, Drosopoulos J H, Price V L, Marcus A J, Maliszewski C R. Elucidation of the thromboregulatory role of CD39/ectoapyrase in the ischemic brain. J Clin Invest 2002; 109:1031-1040
32. Kanthi Y, Hyman M C, Liao H, Baek A E, Visovatti S H, Sutton N R, Goonewardena S N, Neral M K, Jo H, Pinsky D J. Flow-dependent expression of ectonucleotide tri(di)phosphohydrolase-1 and suppression of atherosclerosis. J Clin Invest. 2015; 125: 3027-3036
33. Schönberger T, Ziegler M, Borst O, Konrad I, Nieswandt B, Massberg S, Ochmann C, Jürgens T, Seizer P, Langer H, Münch G, Ungerer M, Preissner K T, Elvers M, Gawaz M P. The platelet collagen receptor GPVI-Fc reduces platelet adhesion to activated endothelium and preserves myocardial function after transient ischemia in mice. Am J Physiol (Cell Physiol.) 2012; 303: C757-C766
34. Göbel S, Li Z M, Vogelmann J, Holthoff H P, Degen H, Hermann D M, Gawaz M, Ungerer M, Münch G. The GPVI-Fc fusion protein Revacept improves cerebral infarct volume and functional outcome in stroke. PLOS ONE 2013: 8:e66960
35. Ungerer M, Li Z M, Baumgartner C, Göbel S, Vogelmann J, Holthoff H P, Bültmann A, Gawaz M, Münch G. The GPVI-Fc fusion protein Revacept reduces thrombus formation and improves vascular dysfunction in atherosclerosis without any impact on bleeding times. PLOS ONE 2013; 8:e71193
36. Bültmann A, Li Z, Wagner S, Peluso M, Schönberger T, Weis C, Konrad I, Stellos K, Massberg S, Nieswandt B, Gawaz M, Ungerer M, Münch G. Impact of glycoprotein VI and platelet adhesion on atherosclerosis—a possible role of fibronectin. J Mol Cell Cardiol 2010; 49: 532-542
37. Jamasbi J, Megens R T A, Bianchini M, Uhland K, Münch G, Ungerer M, Sherman S, Faussner A, Brandl R, John C, Buchner J, Weber C, Lorenz R, Elia N, Siess W. Cross-linking GPVI-Fc by anti-Fc antibodies potentiates its inhibition of atherosclerotic plaque- and collagen-induced platelet activation. J Am Coll Cardiol: Translat Med 2016; 1: 131-142; doi: 10.1016/j.jacbts.2016.03.008
38. Mojica Muñoz A K, Jamasbi J, Degen H, Uhland K, Münch G, Ungerer M, Brandl R, Megens R, Weber C, Lorenz R, Siess W. Recombinant GPVI-Fc added to single or dual antiplatelet therapy in vitro prevents plaque-induced platelet thrombus formation. Thromb Haemost. 2017; 117. Epub ahead of print as of Jun. 1, 2017. doi: 10.1160/TH16-11-0856
39. Newman D K. CD39 target practice. Blood 2013; 121; 3061-3062
40. Jalkanen J, Yegutkin G G, Hollmén M, Aalto K, Kiviniemi T, Salomaa V, Jalkanen S, Hakovirta H. Aberrant circulating levels of purinergic signaling markers are associated with several key aspects of peripheral atherosclerosis and thrombosis. Circ Res 2015; 116: 1206-1215

41. Lecka J, Rana M S, Sevigny J. Inhibition of vascular ectonucleotidase activities by the pro-drugs ticlopidine and clopidogrel favours platelet aggregation. Br J Pharmacol 2010; 161:1150-1160

42. Hohmann J D, Peter K. Activated-platelet targeting of CD39 as a potential way forward. Hämostaseologie 2016: 1: 1-7

43. Fung C Y E, Marcus A J, Broekman M J, Mahaud-Smith M P. P2X1 receptor inhibition and soluble CD39 administration as novel approaches to widen the cardiovascular therapeutic window. Trends Cardiovasc Med 2009; 19:1-5

The invention claimed is:

1. A fusion protein selectively binding collagen and having ectonucleotidase activity, which comprises an extracellular domain of glycoprotein VI, fused via a first linker sequence to the N-terminus of an Fc region, whereby the C-terminus of the Fc region is linked via a second linker sequence to an extracellular domain of a CD39 protein, the fusion protein comprising (a) an amino acid sequence of the extracellular domain of glycoprotein VI with at least 98-99% identical to SEQ ID NO: 2;
(b) an amino acid sequence of an Fc region with at least 98-99% identical to SEQ ID NO: 3;
(c) an amino acid sequence of a CD39 protein with at least 98-99% identical to SEQ ID NO: 4; and
(d) an amino acid sequence of the second linker with at least 98-99% identical to SEQ II) NO: 5.

2. The fusion protein according to claim 1, produced from a host cell deposited with DMSZ under Accession Number DSM ACC3322 (identification reference CHO GPVI-Fc-linker-CD39).

3. The fusion protein according to claim 1, wherein the second linker sequence comprises at least five amino acid residues of SEQ ID NO: 5.

4. The fusion protein according to claim 1, which is a dimer.

5. The fusion protein according to claim 1, which has at least 98-99% identity with amino acid sequence of SEQ ID No.: 1.

6. A polynucleotide comprising a nucleotide sequence that encodes a fusion protein as defined in claim 1.

7. The polynucleotide according to claim 6, which is selected from the group consisting of:
 a) a polynucleotide having a nucleotide sequence of SEQ ID NO: 6;
 b) a polynucleotide having a nucleotide sequence encoding an amino acid sequence at least 98-99% identical to SEQ ID NO: 1; and
 c) a polynucleotide having a nucleotide sequence encoding an amino acid sequence at least 98-99/o identical to SEQ ID NO: 2, SEQ ID NO: 3, or SEQ ID NO: 4.

8. An expression vector comprising a promoter operably associated with the polynucleotide defined in claim 6 or 7.

9. A host cell line transformed or transfected with a polynucleotide as defined by claim 6.

10. The host cell line according to claim 9, which is a stable mammalian cell line, a CHO cell line CHO GPVI-Fc-linker-CD39 deposited with DSMZ under Accession Number DSM ACC 3322 (identification reference CHO GPVI-Fc-linker-CD39).

11. A pharmaceutical composition comprising the fusion protein as defined in claim 1, and a pharmaceutically acceptable carrier.

12. A process for the preparation of a fusion protein, which comprises:
 (a) transforming a host cell comprising at least one vector of claim 8;
 (b) culturing the transformed host cell in suitable conditions for expression of the fusion protein; and
 (c) isolating the fusion protein.

* * * * *

SEQUENCE LISTING

```
<160> NUMBER OF SEQ ID NOS: 7

<210> SEQ ID NO 1
<211> LENGTH: 929
<212> TYPE: PRT
<213> ORGANISM: Homo sapiens

<400> SEQUENCE: 1

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
                100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
        130                 135                 140

Phe Pro Ile Ile Thr Val Thr Ala Ala His Ser Gly Thr Tyr Arg Cys
145                 150                 155                 160

Tyr Ser Phe Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
                180                 185                 190

Pro Thr Glu Pro Pro Ser Ser Val Ala Glu Phe Ser Glu Ala Thr Ala
            195                 200                 205

Glu Leu Thr Val Ser Phe Thr Asn Lys Val Phe Thr Thr Glu Thr Ser
        210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Gly Gly Arg Val Glu Cys Pro
                245                 250                 255

Pro Cys Pro Ala Pro Pro Val Ala Gly Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Gln Phe Asn
        290                 295                 300

Trp Tyr Val Asp Gly Val Glu Val His Asn Ala Lys Thr Lys Pro Arg
305                 310                 315                 320
```

```
Glu Glu Gln Phe Asn Ser Thr Phe Arg Val Ser Val Leu Thr Val
            325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
            355                 360                 365

Gly Gln Pro Arg Glu Pro Gln Val Tyr Thr Leu Pro Pro Ser Arg Glu
            370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys Gly Gly Gly Gly Ser
465                 470                 475                 480

Gly Gly Gly Gly Ser Gly Gly Gly Ser Thr Gln Asn Lys Ala Leu
            485                 490                 495

Pro Glu Asn Val Lys Tyr Gly Ile Val Leu Asp Ala Gly Ser Ser His
            500                 505                 510

Thr Ser Leu Tyr Ile Tyr Lys Trp Pro Ala Glu Lys Glu Asn Asp Thr
            515                 520                 525

Gly Val Val His Gln Val Glu Glu Cys Arg Val Lys Gly Pro Gly Ile
            530                 535                 540

Ser Lys Phe Val Gln Lys Val Asn Glu Ile Gly Ile Tyr Leu Thr Asp
545                 550                 555                 560

Cys Met Glu Arg Ala Arg Glu Val Ile Pro Arg Ser Gln His Gln Glu
            565                 570                 575

Thr Pro Val Tyr Leu Gly Ala Thr Ala Gly Met Arg Leu Leu Arg Met
            580                 585                 590

Glu Ser Glu Glu Leu Ala Asp Arg Val Leu Asp Val Val Glu Arg Ser
            595                 600                 605

Leu Ser Asn Tyr Pro Phe Asp Phe Gln Gly Ala Arg Ile Ile Thr Gly
            610                 615                 620

Gln Glu Glu Gly Ala Tyr Gly Trp Ile Thr Ile Asn Tyr Leu Leu Gly
625                 630                 635                 640

Lys Phe Ser Gln Lys Thr Arg Trp Phe Ser Ile Val Pro Tyr Glu Thr
            645                 650                 655

Asn Asn Gln Glu Thr Phe Gly Ala Leu Asp Leu Gly Gly Ala Ser Thr
            660                 665                 670

Gln Val Thr Phe Val Pro Gln Asn Gln Thr Ile Glu Ser Pro Asp Asn
            675                 680                 685

Ala Leu Gln Phe Arg Leu Tyr Gly Lys Asp Tyr Asn Val Tyr Thr His
            690                 695                 700

Ser Phe Leu Cys Tyr Gly Lys Asp Gln Ala Leu Trp Gln Lys Leu Ala
705                 710                 715                 720

Lys Asp Ile Gln Val Ala Ser Asn Glu Ile Leu Arg Asp Pro Cys Phe
            725                 730                 735
```

```
His Pro Gly Tyr Lys Lys Val Val Asn Val Ser Asp Leu Tyr Lys Thr
            740                 745                 750

Pro Cys Thr Lys Arg Phe Glu Met Thr Leu Pro Phe Gln Gln Phe Glu
            755                 760                 765

Ile Gln Gly Ile Gly Asn Tyr Gln Gln Cys His Gln Ser Ile Leu Glu
            770                 775             780

Leu Phe Asn Thr Ser Tyr Cys Pro Tyr Ser Gln Cys Ala Phe Asn Gly
785                 790                 795                 800

Ile Phe Leu Pro Pro Leu Gln Gly Asp Phe Gly Ala Phe Ser Ala Phe
                805                 810                 815

Tyr Phe Val Met Lys Phe Leu Asn Leu Thr Ser Glu Lys Val Ser Gln
            820                 825                 830

Glu Lys Val Thr Glu Met Met Lys Lys Phe Cys Ala Gln Pro Trp Glu
            835                 840                 845

Glu Ile Lys Thr Ser Tyr Ala Gly Val Lys Glu Lys Tyr Leu Ser Glu
            850                 855                 860

Tyr Cys Phe Ser Gly Thr Tyr Ile Leu Ser Leu Leu Gln Gly Tyr
865                 870                 875                 880

His Phe Thr Ala Asp Ser Trp Glu His Ile His Phe Ile Gly Lys Ile
                885                 890                 895

Gln Gly Ser Asp Ala Gly Trp Thr Leu Gly Tyr Met Leu Asn Leu Thr
                900                 905                 910

Asn Met Ile Pro Ala Glu Gln Pro Leu Ser Thr Pro Leu Ser His Ser
            915                 920                 925

Thr

<210> SEQ ID NO 2
<211> LENGTH: 249
<212> TYPE: PRT
<213> ORGANISM: Homo sapiens
<220> FEATURE:
<221> NAME/KEY: CHAIN
<222> LOCATION: (1)..(249)

<400> SEQUENCE: 2

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
            115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160
```

```
Tyr Ser Phe Ser Ser Arg Asp Pro Tyr Leu Trp Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn
                245
```

<210> SEQ ID NO 3
<211> LENGTH: 223
<212> TYPE: PRT
<213> ORGANISM: Homo sapiens
<220> FEATURE:
<221> NAME/KEY: CHAIN
<222> LOCATION: (1)..(223)

<400> SEQUENCE: 3

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 4
<211> LENGTH: 439
<212> TYPE: PRT
<213> ORGANISM: Homo sapiens
<220> FEATURE:
<221> NAME/KEY: CHAIN
<222> LOCATION: (1)..(439)

<400> SEQUENCE: 4

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65              70                  75                  80

Arg Ser Gln His Gln Glu Thr Pro Val Tyr Leu Gly Ala Thr Ala Gly
            85                  90                  95

Met Arg Leu Leu Arg Met Glu Ser Glu Leu Ala Asp Arg Val Leu
        100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365

Glu Lys Tyr Leu Ser Glu Tyr Cys Phe Ser Gly Thr Tyr Ile Leu Ser
370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
```

```
                    405                 410                 415
Tyr Met Leu Asn Leu Thr Asn Met Ile Pro Ala Glu Gln Pro Leu Ser
            420                 425                 430

Thr Pro Leu Ser His Ser Thr
        435

<210> SEQ ID NO 5
<211> LENGTH: 15
<212> TYPE: PRT
<213> ORGANISM: Homo sapiens
<220> FEATURE:
<221> NAME/KEY: CHAIN
<222> LOCATION: (1)..(15)

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 2847
<212> TYPE: DNA
<213> ORGANISM: Homo sapiens
<220> FEATURE:
<221> NAME/KEY: gene
<222> LOCATION: (1)..(2847)

<400> SEQUENCE: 6
```

| | | | | |
|---|---|---|---|---|
| atggaaaccc | ctgctcagct | gctgttcctg | ctgctgctgt | ggctgcctga | caccaccggc | 60 |
| cagtccggac | tctgcctaa | gccttccctg | caggccctgc | cttcctccct | ggtgcctctg | 120 |
| gaaaagcctg | tgaccctgag | gtgtcaggga | cctcctggcg | tggacctgta | ccggctggaa | 180 |
| aagctgtcct | ccagcagata | ccaggaccag | gccgtgctgt | tcatccctgc | catgaagcgg | 240 |
| tccctggccg | gcaggtacag | gtgctcctac | cagaacggct | ccctgtggtc | tctgccttct | 300 |
| gaccagctgg | aactggtggc | taccggcgtg | ttcgccaagc | cttctctgtc | tgcccagcct | 360 |
| ggacctgctg | tctcctctgg | aggcgacgtg | acactgcagt | gccagaccag | atacggcttc | 420 |
| gatcagttcg | ccctgtacaa | agagggcgac | cctgccccct | acaagaaccc | tgagcggtgg | 480 |
| tacagggcct | ccttccctat | catcaccgtg | accgccgctc | actccggcac | ctaccggtgc | 540 |
| tacagcttct | cctcccggga | cccttacctg | tggtccgccc | ctagcgaccc | tctcgaactg | 600 |
| gtcgtcaccg | gaacctccgt | gacccctcc | aggctgccta | ccgagcctcc | tagctccgtg | 660 |
| gccgagttct | ctgaggccac | cgccgagctg | accgtgtcct | tcaccaacaa | ggtgttcacc | 720 |
| accgagacat | cccggtccat | caccacctcc | cccaaagagt | ccgactctcc | tgccggccct | 780 |
| gctcggcagt | actacaccaa | gggcaacggc | ggcagagtgg | agtgtcctcc | ttgccctgcc | 840 |
| cctcctgtgg | ctggcccttc | cgtgttcctg | ttccctccaa | agcctaagga | caccctgatg | 900 |
| atctcccgga | cccctgaagt | gacctgcgtg | gtggtggacg | tgtcccacga | ggaccctgag | 960 |
| gtgcagttca | ttggtacgt | ggacggcgtg | gaggtgcaca | acgccaagac | caagcctcgg | 1020 |
| gaggaacagt | tcaactccac | cttccgggtg | gtgtccgtgc | tgaccgtggt | gcaccaggac | 1080 |
| tggctgaacg | gcaaagaata | caagtgcaag | gtgtccaaca | agggcctgcc | tgcccctatc | 1140 |
| gaaaagacca | tcagcaagac | caagggacag | cctcgcgagc | ctcaggtgta | caccctgcct | 1200 |
| ccaagccggg | aggaaatgac | caagaaccag | gtgtccctga | cctgcctggt | caagggcttc | 1260 |
| taccctccg | atatcgccgt | ggagtgggag | tctaacggcc | agcctgagaa | caactacaag | 1320 |
| accaccccctc | ctatgctgga | ctccgacggc | tccttcttcc | tgtactccaa | actgaccgtg | 1380 |

```
gacaagtccc ggtggcagca gggcaacgtg ttctcctgct ccgtgatgca cgaggccctg    1440
cacaaccact acacccagaa gtccctgtcc ctgtctcctg caagggtgg aggcggttca     1500 ggcggaggtg gcagcggcgg tggcggatcg acccagaaca aggccctgcc tgagaacgtg    1560
aagtacggca tcgtgctgga tgctggctcc tcccacacct ccctgtacat ctacaagtgg    1620
cctgccgaga agaaaacga caccggcgtg gtgcaccagg tggaggaatg cagagtgaag     1680
ggccctggca tctccaagtt cgtgcagaaa gtgaacgaga tcggcatcta cctgaccgac    1740
tgcatggaac gggccaggga agtgatccct cggtcccagc atcaggaaac ccccgtctac    1800
ctgggcgcta ccgccggcat gcggctgctg cggatggaat ccgaggaact ggccgacagg    1860
gtgctggacg tggtggagcg gtccctgtcc aactacccat tcgactttca gggcgccagg    1920
atcatcaccg ccaggaaga gggcgcttac ggctggatca ccatcaacta cctgctgggc     1980
aagttctccc agaaaacccg gtggttctcc atcgtgccct acgagacaaa caaccaggaa    2040
accttcggcg ctctggatct gggcggagcc tctacccagg tgaccttcgt gcctcagaac    2100
cagaccatcg agtccccga caacgccctg cagttccggc tgtacggcaa ggactacaac    2160
gtgtacaccc acagctttct gtgctatggc aaggaccagg ccctgtggca gaagctggcc    2220
aaggacatcc aggtggcctc caacgagatc ctgcgggacc cttgcttcca ccctggctac    2280
aagaaagtgg tgaacgtgtc cgacctgtac aagaccctt gcaccaagcg gttcgagatg     2340
accctgcctt ccagcagtt cgagatccag ggcatcggca actaccagca gtgccaccag     2400
tccatcctgg aactgttcaa caccagctac tgcccttact cccagtgcgc cttcaacggc    2460
atcttcctgc cccctctgca gggcgacttc ggcgccttct ccgccttcta cttcgtgatg    2520
aagttcctga acctgacctc cgagaaggtg tcccaagaaa aagtgaccga tgatgaag     2580 aagttctgcg cccagccttg ggaggaaatc aagacctcct acgctggcgt gaaagagaag    2640
tacctgtccg agtactgctt ctccggcacc tacatcctgt ctctgctgct gcagggctac    2700
cacttcaccg ccgactcttg ggagcacatc cacttcatcg gcaagatcca gggaagcgac    2760
gccggctgga ccctgggcta catgctgaat ctgaccaaca tgatccctgc cgagcagcct    2820
ctgtccaccc ctctgtccca ctccacc                                        2847
```

<210> SEQ ID NO 7
<211> LENGTH: 20
<212> TYPE: PRT
<213> ORGANISM: Homo sapiens
<220> FEATURE:
<221> NAME/KEY: SIGNAL
<222> LOCATION: (1)..(20)

<400> SEQUENCE: 7

```
Met Glu Thr Pro Ala Gln Leu Leu Phe Leu Leu Leu Leu Trp Leu Pro
1               5                   10                  15

Asp Thr Thr Gly
            20
```